(12) United States Patent
Bottaro et al.

(10) Patent No.: US 7,132,392 B1
(45) Date of Patent: *Nov. 7, 2006

(54) INHIBITION OF CELL MOTILITY AND ANGIOGENESIS BY INHIBITORS OF GRB2-SH2-DOMAIN

(75) Inventors: Donald P. Bottaro, Kensington, MD (US); Safiye N. Atabey, Izmir (TR); Jesus V. Soriano, Washington, DC (US); Diane E. Breckenridge, Kensington, MD (US); Zhu-Jun Yao, Shanghai (CN); Yang Gao, Branford, CT (US); Terrence R. Burke, Jr., Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 559 days.

This patent is subject to a terminal disclaimer.

(21) Appl. No.: 10/111,192

(22) PCT Filed: Oct. 20, 2000

(86) PCT No.: PCT/US00/41423

§ 371 (c)(1), (2), (4) Date: Apr. 22, 2002

(87) PCT Pub. No.: WO10/28577

PCT Pub. Date: Apr. 26, 2001

Related U.S. Application Data

(60) Provisional application No. 60/160,899, filed on Oct. 22, 1999, provisional application No. 60/221,525, filed on Jul. 28, 2000.

(51) Int. Cl.
| | |
|---|---|
| A61K 38/08 | (2006.01) |
| A61K 38/07 | (2006.01) |
| A61K 38/06 | (2006.01) |
| C07K 7/04 | (2006.01) |
| C07K 5/10 | (2006.01) |
| C07K 5/08 | (2006.01) |

(52) U.S. Cl. .................. 514/2; 530/300; 530/329; 530/330; 530/331; 514/16; 514/17; 514/18; 514/19

(58) Field of Classification Search ............. 514/2; 530/300, 345
See application file for complete search history.

(56) References Cited

U.S. PATENT DOCUMENTS

| | | | |
|---|---|---|---|
| 3,906,031 A | 9/1975 | Carpino et al. |
| 4,394,519 A | 7/1983 | Carpino et al. |
| 4,879,398 A | 11/1989 | Getman et al. |
| 5,182,263 A | 1/1993 | Danho et al. |
| 5,200,546 A | 4/1993 | Burke, Jr. et al. |
| 5,272,268 A | 12/1993 | Toyoda et al. |
| 5,296,608 A | 3/1994 | Danho et al. |
| 5,369,110 A | 11/1994 | Schmidlin et al. |
| 5,457,114 A | 10/1995 | Stüber et al. |
| 5,463,062 A | 10/1995 | Hemmerle et al. |
| 5,491,253 A | 2/1996 | Stuk et al. |
| 5,508,437 A | 4/1996 | Danho et al. |
| 5,525,733 A | 6/1996 | Novack et al. |
| 5,580,979 A | 12/1996 | Bachovchin |
| 5,587,372 A | 12/1996 | Aszodi et al. |
| 5,612,370 A | 3/1997 | Atwal |
| 5,616,776 A | 4/1997 | Stuk et al. |
| 5,627,283 A | 5/1997 | Stüber et al. |
| 5,646,036 A | 7/1997 | Schwall et al. |
| 5,679,842 A | 10/1997 | Kleiner |
| 5,686,292 A | 11/1997 | Schwall et al. |
| 5,688,992 A | 11/1997 | Burke, Jr. et al. |
| 5,698,731 A | 12/1997 | Bosetti et al. |
| 5,707,624 A | 1/1998 | Nickoloff et al. |
| 5,710,129 A | 1/1998 | Lynch et al. |
| 5,710,173 A | 1/1998 | Tang et al. |
| 5,712,395 A | 1/1998 | App et al. |
| 5,753,687 A | 5/1998 | Mjalli et al. |
| 5,756,817 A | 5/1998 | Choi et al. |
| 5,773,411 A | 6/1998 | Wells et al. |
| 5,780,496 A | 7/1998 | Tang et al. |
| 5,786,454 A | 7/1998 | Waksman et al. |
| 5,789,427 A | 8/1998 | Chen et al. |
| 5,792,771 A | 8/1998 | App et al. |
| 5,792,783 A | 8/1998 | Tang et al. |
| 5,834,504 A | 11/1998 | Tang et al. |
| 5,843,997 A | 12/1998 | Heinz et al. |
| 5,849,693 A | 12/1998 | Wells et al. |
| 5,849,742 A | 12/1998 | App et al. |
| 5,880,141 A | 3/1999 | Tang et al. |
| 5,883,110 A | 3/1999 | Tang et al. |
| 5,883,113 A | 3/1999 | Tang et al. |
| 5,883,116 A | 3/1999 | Tang et al. |
| 5,886,020 A | 3/1999 | Tang et al. |
| 5,886,195 A | 3/1999 | Tang et al. |
| 5,891,917 A | 4/1999 | Tang et al. |
| 5,912,183 A | 6/1999 | Comoglio et al. |
| 5,935,993 A | 8/1999 | Tang et al. |
| 5,958,957 A | 9/1999 | Andersen et al. |
| 5,965,558 A | 10/1999 | Mjalli et al. |
| 5,972,978 A | 10/1999 | Andersen et al. |
| 5,981,569 A | 11/1999 | App et al. |
| 6,037,134 A | 3/2000 | Margolis |
| 6,228,986 B1 | 5/2001 | Lanter et al. |
| 6,307,090 B1 * | 10/2001 | Burke et al. .............. 560/76 |

FOREIGN PATENT DOCUMENTS

| | | |
|---|---|---|
| WO | WO 94/07913 | 4/1994 |
| WO | WO 95/11917 | 5/1995 |
| WO | WO 96/23813 | 8/1996 |
| WO | WO 97/08193 | 3/1997 |
| WO | WO 9708193 A1 * | 3/1997 |
| WO | WO 00/56760 | 9/2000 |
| WO | WO 00/73326 | 12/2000 |

OTHER PUBLICATIONS

Yao Z-J, King CR, Cao, T, Kelley J, Milne GWA, Voight JH, Burke TR. Potent Inhibition of Grb2 SH2 Domain Binding by Non-Phosphate-Containing Ligands. J. Med. Chem. 1999, 42, 25-35.*
RS Herbst. Int. J. Radiation Oncology Biol. Phys. (2004) 59, 21-26.*
ML Janmaat and G Giaccone. The Oncologist (2003), 8, 576-586.*
F-DT Lung and J-Y Tsai. Biopolymers (2003) 71, 132-140.*

M Ranson. British J. Cancer (2004) 90, 2250-2255.*
Falm Eskens. British J. Cancer (2004) 90, 1-7.*
J Dancey. Int. J. Radiation Oncology Biol. Phys. (2004) 58, 1003-1007.*
L Oligino, et al. J. Biol. Chem. (1997) 272, 29046-29052.*
Y Gao, et al. J. Med. Chem. (2000) 43, 911-920.*
B Gay, et al. Int. J. Cancer (1999) 83, 235-241.*
P Furet, et al. J. Med. Chem. (1998) 41, 3442-3449.*
Z-J Yao, et al. J. Med. Chem.(1999) 42, 25-35.*
Webster's Online Dictionary. Accessed Oct. 1, 2004 at http://machaut.uchicago.edu/cgi-bin/WEBSTER.sh?WORD=oxalyl.*
SIGMA. Designing Custom Peptides. http://www.sigma-genosys.com/peptide_design.asp (Accessed Dec. 16, 2004). 2 pages.*
HJC Berendsen. A Glimpse of the Holy Grail? Science (1998) 282. 642-643.*
D Voet and JG Voet. Biochemistry, 2nd Edition.(1995). 235-241.*
DE Smilek, et al. A single amino acid . . . Proc. Natl. Acad. Sci. USA (1991) 88.9633-9637.*
Z-J Yao, et al. J. Med. Chem. (1999) 42, 25-35.*
HJC Berendsen. A Glimpse of the Holy Grail? Science (1998) 282. 642-643.*
D Voet and JG Voet. Biochemistry, 2nd Edition.(1995). 235-241.*
DE Smilek, et al. A single amino acid . . . Proc. Natl. Acad. Sci. USA (1991) 88. 9633-9637.*
J. Rudinger. In: Peptide Hormones, JA Parsons, Ed. (1976) 1-7.*
W.S. Messer, "Vasopressin and Oxytocin", web document updated Apr. 3, 2000; http://www.neurosci.pharm.utoledo.edu/MBC3320/vasopressin.htm; 5 pages.*
Ye et al., "L-O-(2-Malonyl)tyrosine" A New Phosphotyrosyl Mimetic for the Preparation of Src Homology 2 Domain Inhibitory Peptides, J. Med. Chem. vol. 38, pp. 4270-4275, 1995.
Burke, Jr., et al., "4'-O-[2-(2-Fluoromalonyl)]-L-tyrosine: A Phosphotyrosyl Mimic for the Preparation of Signal Transduction Inhibitory Peptides", J. Med. Chem., vol. 39, pp. 1021-1027, Mar. 1, 1996.
Schoepfer et al., "Structure-based Design of Peptidomimetic Ligands of Grb2-SH2 Domain", Bioorganic & Medicinal Chemistry Letters 8, pp. 2865-2870, 1998.
Yao et al., "Potent Inhibition of Grb2 SH2 Domain Binding by Non-Phosphate-Containing Ligands", J. Med. Chem., vol. 42, pp. 25-35, 1999.
Gay et al., "Effect of Potent and Selective Inhibitors of the Grb2 SH2 Domain on Cell Motility", The Journal of Biological Chemistry, vol. 274, pp. 23311-23315, Aug. 13, 1999.
Schoepfer et al., "Highly Potent Inhibitors of the Grb2-SH2 Domain", Bioorganic & Medicinal Chemistry Letters 9, pp. 211-226, 1999.
Burke, Jr., et al., Monocarboxylic-Based Phosphotyrosyl Mimetics in the Design of Grb2 SH2 Domain Inhibitors, Bioorganic & Medicinal Chemistry Letters 9, pp. 347-352, 1999.
Gilmer et al., "Peptide Inhibitors of src SH3-SH2-Phosphorprotein Interactions", The Journal of Biological Chemistry, vol. 269, pp. 31711-31719, Dec. 16, 1994.
Charifson et al., "Peptide Ligands of pp60$^{c-src}$ SH2 Domains: A Thermodynamic and Structural Study", Biochemistry, vol. 36, pp. 6283-6293, 1997.
Liu et al., "Synthesis of L-2,3,5,6-Tetrafluoro-4-(Phosphonomethyl) Phenylalanine, a Novel Non-Hydrolyzable Phosphotyrosine Mimetic and L-4-(Phosphonodifluoromethyl)Phenylalanine", Tetrahedron Letters, vol. 38, pp. 1389-1392, 1997.
Cleland, "The Meerwein Reaction in Amino Acid Synthesis. II. An Investigation of Twenty-one Substituted Anilines", The Journal of Organic Chemistry, Vo., 34, pp. 744-747, Mar. 1969.
Gao et al., Inhibition of Grb2 SH2 Domain Binding by Non-Phosphate-Containing Ligands. 2. 4-(2-Malonyl)phenylalamine as a Potent Phosphotyrosyl Mimetic, J. Med. Chem., vol. 43, pp. 911-920, 2000.
Furet et al., Structure-Based Design and Synthesis of High Affinity Tripeptide Ligands of the Grb2-SH2 Domain, J. Med. Chem., vol. 41, pp. 3442-3449, 1998.
Tong et al., "Carboxymethyl-phenylalanine as a Replacement for Phosphotyrosine in SH2 Domain Binding", The Journal of Biological Chemistry, vol. 273, pp. 20238-20242 Aug. 7, 1998.
Kim et al., FEBS Lett, 453, 174-178, 1999.
Tulasne et al., "The Multisubstrate Docketing Site of the MET Receptor is Dispensable for MET-mediated RAS Signaling and Cell Scattering", Molecular Biology of the Cell, vol. 10, pp. 551-565, Mar. 1999.

Kim et al., "Dual Signaling Role of the Protein Tyrosine Phosphotase SHP-2 in Regulating Expression of Acute-Phase Plasma Proteins by Interleukin-6 Cytokine Receptors in Hepatic Cells", Molecular and Cellular Biology, vol. 19, pp. 5326-5338, Aug. 1999.
Nguyen et al., "Association of the Multisubstrate Docking Protein Gab1 with the Hepatocyte Growth Factor Receptor Requires a Functional Grb2 Binding Site Involving Tyrosine 1356", The Journal of Biological Chemistry, vol. 272, pp. 20811-29819, Aug. 15, 1997.
Maina et al., "Uncoupling of Grb2 from the Met Receptor in Vivo Reveals Complex roles in Muscle Development", Cell, vol. 87, pp. 531-542, Nov. 1, 1996.
Ponzetto et al., "Specific Uncoupling of GRB2 from the Met Receptor", The Journal of Biological Chemistry, vol. 271, pp. 14119-14123, Jun. 14, 1996.
Ettmayer et al., "Structural and Conformational Requirements for High-Affinity Binding to the SH2 Domain of Grb2", J. Med. Chem., vol. 42, pp. 971-980, 1999.
Royal et al., "Differential Requirement of Grb2 and P13-Kinase in HGF/SF-Induced Cell Motility and Tubulogenesis", Journal of Cellular Physiology, vol. 173, pp. 196-201, 1997.
Gao et al., Biorg & Med Chem Lett, 10, 923-927 (2000).
Burke, Jr., et al., "Preparation of . . . Peptide Synthesis", J. of Synthetic Organic Chem., No. 11, p. 1019, Nov. 11, 1991.
Burke, Jr., et al., "Potent Inhibition of Grb2 SH2 domain Binding by Non-Phosphate containing Ligands", First Annual Meeting on the Experimental Therapeutics of Human Cancer, Jun. 11-13, 1998, Hood College, Frederick Maryland (Summary).
Katunuma et al., "Use of new synthetic substrates for assays of cathepsin L and cathepsin B", J. Biochem. (Tokyo), vol. 93, pp. 1129-1135, 1983 (Abstract only).
Burke, Jr., et al., "Enantioselective Synthesis . . . Inhibitory Peptides", Tetrahedron, vol. 54, pp. 9981-9994, 1998.
Burke, Jr., et al., "Phosphotyrosyl-Based Motifs in the Structure-Based Design of Protein-Tyrosine Kinase-Dependent Signal Transduction Inhibitors", Current Pharmaceutical Design, vol. 3, pp. 291-304, 1997.
Burke, Jr., et al., "Nonhydrolyzable Phosphotyrosyl Mimetics for the Preparation of Phosphatase-Resistant SH2 Domain Inhibitors", Biochemistry, vol. 33, pp. 6490-6494, 1994.
Ye et al., "L-O-(2-Malonyl)tyrosine (L-OMT) a New Phosphotyrosyl Mimic Suitably Protected for Solid-Phase Synthesis of Signal Transduction Inhibitory Peptides", Tetrahedron Letters, vol. 36, pp. 4733-4736, 1995.
Kuriyan, "Modular Peptide recognition Domains in Eukaryotic Signaling", Annu. Rev. Biophys. Biomol. Struct., vol. 26, pp. 259-288, 1997.
Mayer et al., "Functions of SH2 AND SH3 Domains", Protein modules in signal transduction, edited by A. J. Pawson, Berlin, New York, Springer, c1998, pp. 1-22.
Fry et al., "New insights into protein-tyrosine kinase receptor signaling complexes", Protein Science, vol. 2, pp. 1785-1797, 1993.
Levitzki, "Targeting signal transduction for disease therapy", Current Opinion in Cell Biology, vol. 8, pp. 239-244, 1996.
Boutin, "Tyrosine Protein Kinase Inhibition and Cancer", Int. J. Biochem., vol. 26, pp. 1203-1226, 1994.
Levitzki et al., "Tyrosine Kinase Inhibition: An Approach to Drug Development", Science, vol. 267, pp. 1782-1788, Mar. 24, 1995.
Lawrence et al., "Protein Kinase Inhibitors: The Tyrosine-specific Protein Kinases", Pharmacol. Ther., vol. 77, pp. 81-114, 1998.
Burke, Jr., et al., "Protein-Tyrosine Phosphatases: Structure, Mechanism, and Inhibitor Discovery", Biopolymers (Peptide Science), vol., 47, pp. 225-241 (1998).
Schoelson, "SH2 and PTB domain interactions in tyrosine kinase signal transduction", Current Opinion in Chemical Biology, vol. 1, pp. 227-234, 1997.
Waksman et al., "Crystal structure of the phosphotyrosine recognition domain Sh2 of v-src complexed with tyrosine-phosphorylated peptides", Nature, vol. 358, pp. 646-653, Aug. 20, 1992.
Waksman et al., "Binding of High Affinity Phosphotyrosyl Peptide to the Src SH2 Domain: Crystal Structures of the Complexed and Peptide-free Forms", Cell, vol. 72, pp. 779-790, Mar. 12, 1993.
Mikol et al., "The Crystal Structures of the SH2 Domain of p56$^{lck}$ Complexed with Two Phosphonopeptides Suggest a Gated Peptide Binding Site", J. Mol. Biol. vol. 246, pp. 344-355, 1995.

Hatada et al., "Molecular basis for interaction of the protein tyrosine kinase ZAP-70 with the T-cell receptor", Nature, vol. 377, pp. 32-38, Sep. 7, 1995.
Zhou et al., "Solution structure of the Shc SH2 domain complexed with a tryrosine-phosphorylated peptide from the T-cell receptor", Proc. Natl. Acad. Sci., vol. 92, pp. 7784-7788, Aug. 1995.
Narula et al., "Solution structure of the C-terminal SH2 domain of the human tyrosine kinase Syk complexed with a phosphotyrosine pentapeptide", Structure, vol. 3, 1061-1073, Oct. 15, 1995.
Xu et al., "Solution Structure of the Human pp60$^{c\text{-}src}$ SH2 Domain Complexed with a Phosphorylated Tyrosine Pentapeptide", Biochemistry, vol. 34, pp. 2107-2121, 1995.
Tong et al., "Crystal Structures of the Human p56$_{lck}$ SH2 Domain in Complex with Two Short Phosphotyrosyl Peptides at 1.0 Å and 1.8 Å Resolution", Academic Press Limited, 10 pages, 1996.
Sicheri et al., "Crystal structure of the Src family tyrosine kinase Hck", Nature, vol. 385, pp. 602-609, Feb. 13, 1997.
Chen et al., "Crystal Structure of a Tyrosine Phosphorylated STAT-1 Dimer Bound to DNA", Cell, vol. 93, pp. 827-839, May 29, 1998.
Songyang et al., "Recongnition and specificity in protein tyrosine kinase-medicated signalling", Elsevier Science Ltd., pp. 470-475, 1995.
Lunney et al., "Structure-Based Design of a Novel Series of Nonpeptide Ligands That Bind to the pp60$^{src}$ SH2 Domain", J. Am. Chem. Soc., vol. 119, pp. 12471-12476, 1997.
Pacofsky et al., "Potent Dipeptide Inhibitors of the pp60$^{c\text{-}src}$ SH2 Domain", J. Med. Chem., vol. 41, pp. 1894-1908, 1998.
Marseigne et al., "Synthesis of New Amino Acids Mimicking Sulfated and Phosphorylated Tyrosine Residues", J. Org. Chem., vol. 53, pp. 3621-3624, 1988.
Domchek et al., "Inhibition of SH2 Domain/Phosphoprotein Association by a Nonhydrolyzable Phosphonopeptide", Biochemistry, vol. 31, pp. 9865-9870, 1992.
Xiao et al., "Syp (SH-PTP2) Is a Positive Mediator of Growth Factor-stimulated Mitogenic Signal Transduction", The Journal of Biological Chemistry, vol. 269, pp. 21244-21248, Aug. 19, 1994.
Wange et al., "F$_2$(Pmp)$_2$-TAMζ$_3$, a Novel Competitive Inhibitor of the binding of ZAP-70 to the T Cell Antigen Receptor, Blocks Early T Cell Signaling", JBC Online, vol. 270, pp. 944-948, Jan. 13, 1995.
Rojas et al., "Controlling Epidermal Growth Factor (EGF)-stimulated RAS Activation in Intact Cells by a Cell-permeable Peptide Mimicking Phosphorylated EGF Receptor", The Journal of Biological Chemistry, vol. 271, pp. 27456-27461, Nov. 1, 1996.
Williams et al., "Selective Inhibition of Growth Faxtor-stimulated Mitogenesis by a Cell-permeable Grb2-binding Peptide", The Journal of Biological Chemistry, vol. 272, pp. 22349-22354, Aug. 29, 1997.
Stankovic, "The Role of 4-Phosphonodifluoromethyl- and 4-Phosphono-Phenylalanine in the Selectivity and Cellular Uptake of SH2 domain Ligands", Bioorganic & Medicinal Chemistry Letters, vol. 7, pp. 1909-1914, 1997.
Mehrotra et al., "α-Dicarbonyls as "Non-Charged" Arginine-Directed Affinity Labels", Bioorganic & Medicinal Chemistry Letters, vol. 6, pp. 1941-1946, 1996.
Margolis, "The GRB Family of SH2 domain Proteins", Prog. Biophys. Molec. Biol., vol. 62, pp. 223-244, 1994.
Burke, Jr., et al., "Preparation of Fluoro- and Hydroxy-4-(phosphonomethyl)-D,L-phenylalanine Suitably Protected for Solid-Phase Synthesis of Peptides Containing Hydrolytically Stable Analogues of O-Phosphotyrosine", Jour. Of Organic Chemistry, pp. 1336-1340, Mar. 12, 1993.
Burke, Jr., et al., "Synthesis of 4-Phosphono(difluoromethyl)-D,L-phenyllanine and N-Boc and N-Fmoc Derivatives Suitably Protected for solid-Phase Synthesis of Nonhydrolyzable Phosphotyrosyl Peptide Analogues", Tetrahedron Letters, vol. 34, pp. 4125-4128, 1993.
Smyth et al., "Enanthioselective Synthesis of N-Boc and N-Fmoc Protected Diethyl 4-Phosphono(difluoromethyl)-L-Phenylalanine; Agents Suitable for the Solid-Phase Synthesis of Peptides Containing Nonhydrolyzable Analogues of O-Phosphotyrosine", Tetrahedron letters, vol. 35, pp. 551-554, 1994.
Miller et al., "EPSP Synthase . . . 3-Phosphate Mimics", J. Organic & Medicinal Chem. Letters, vol. 3, No. 7, pp. 1435-1440, 1993.
"Synthesis and . . . containing peptides", Chem. Abs., vol. 123, No. 257331h, p. 1220, 1995.
Furet et al., "Discovery of 3-Aminobenzyloxycarbonyl as an N-Terminal Group conferring High Affinity to the Minimal Phosphopeptide Sequence Recognized by the Grb2-SH2 Domain", J. Med. Chem., vol. 40, pp. 3551-3556, 1997.
Rahuel et al., "Structural Basis for the High Affinity of Amino-Aromatic SH2 Phosphopeptide Ligands", J. Mol. Biol., 279, pp. 1013-1022, 1998.
Garcia-Echeverria et al., "Potent Antagonists of the SH2 Domain of Grb2: Optimization of the X$_{+1}$-Position of 3-Amino-Z-Tyr(PO$_3$H$_2$)-X$_{=1}$-Asn-NH$_2$", Journal of Medicinal Chemistry, vol. 41, pp. 1741-1744, May 21, 1998.
Rahuel et al., "Structural basis for specificty of GRB2-SH2 revealed by a novel ligand binding mode", Nature Structural Biology, vol. 3, No. 7, pp. 586-589, Jul. 7, 1996.
Oligino et al., "Nonphosphorylated . . . 2 Domain", The J. of Biological Chem., vol. 272, No. 46, pp. 29046-29052, Nov. 14, 1997.
Allen et al., "Tritiated Peptides. Part 15. Synthesis of Tritium Labelled Biologically Active Analogues of Somatostatin", J. Chem. Soc., Perkin Trans. 1, pp. 989-1003, 1986.
Ben-Levy et al., "A single autophosphorylation site confers oncongenicity to the Neu/ErbB-2 receptor and enables coupling to the MAP Kinase pathway", The EMBO Journal, vol. 13, pp. 3302-3311, 1994.
Dankort et al., Distinct Tyrosine Autophosphorylation Sites Negatively and Positively Modulate New-Mediated Transformation, Molecular and Cellular Biology, vol. 17, pp. 5410-5425, Sep. 1997.
Ma et al., "Bcr phosphorylated on tyrosine 177 binds Grb2", Oncogene, vol. 14, pp. 2367-2372, 1997.
DiFiore et al., "Overexpression of the Human EGF Receptor confers an EGF-Dependent Transformed Phenotype to NIH 3T3 Cells", Cell, vol. 51, pp. 1063-1070, Dec. 24, 1987.
Hudziak et al, "Increased expression of the putative growth factor receptor p185$^{HER2}$ causes transformation and tumorigenesis of NIH 3T3 cells", Proc. Natl. Acad. Sci., vol. 84, pp. 7159-7163, Oct. 1987.
Kraus et al., "Overexpression of the EGF receptor-related photo-oncogene erbB-2 in human mammary tumor cells lines by different molecular mechanisms", The EMBO Journal, vol. 6, pp. 605-610, 1987.
Sastry et al., "Quantitative analysis of Grb2-Sos1 interaction: the N-terminal SH3 domain of Grb2 mediates affinity", Oncogene, 11, pp. 1107-1112, 1995.
Searles, The Reaction of Trimethylene Oxide with Grignard Reagents and Organolithium Compounds, J. Amer. Chem. Soc., vol. 73, pp. 124-125, 1951.
Fretz et al., "Targeting a Hydrophobic Patch on the Surface of the Grb2-SH2 Domain", 15$^{th}$ Amer. Peptide Symposium, Nashville, TN, Jun. 1997, Abstract No. P422.
Fixman et al., "Efficient Cellular . . . Proteins, Cb1 and Gab1", The J. of Biological Chem., vol. 272, No. 32, pp. 20167-20172, Aug. 8, 1997.
Tari et al., "Inhibition of Grb2 . . . Leukemic Cells", Biochemical and Biophysical Research Communications, vol. 235, pp. 383-388, Article No. RC976791, 1997.
Xie et al., "Dominant-negative Mutants . . . Rat HER-2/Neu", The J. of Biological Chem., vol. 270, No. 51, pp. 30717-30724, Dec. 22, 1995.
Maignan et al., "Crystal Structure of the Mammalian Grb2 Adaptor", Science, vol. 268, pp. 291-293, Apr. 14, 1995.
Saltiel et al. "Targeting signal transduction in the discovery of antiproliferative drugs", Chemistry & Biology, vol. 3, No. 11, pp. 887-893, Nov. 1996.
McNemar et al., Thermodynamic and . . . Binding to Grb2-SH2:, Biochemistry, vol. 36, pp. 10006-10014, 1997.
Ogura et al., "Conformation of an . . . Grb2 SH2 domain", J. of Biomolecular NMR, vol. 10, pp. 273-278, 1997.
Gay et al., "Dual Specificity of . . . Peptide Ligands", Biochemistry, vol. 36, pp. 5712-5718, 1997.
Bobko et al., "CD45 Protein . . . Irreversible Inhibitors", Bioorganic & Medicinal Chem. Letters, vol. 5, No. 4, pp. 353-356, 1995.
Burke et al., "Conformationally Constrained . . . 2 Domain Inhibitors", J. Med. Chem., vol. 38, pp. 1386-1396, 1995.
Chemical Abstracts, vol. 122, p. 424, 1995 (Abs. No. 258899).
Gordeev et al., "N-α-Fmoc-4-Phosphono(difluoromethyl)-L-phenylalanine: . . . into Peptides", Tetrahedron Letters, vol. 35, pp. 7585-7588, 1994.
Kitas et al., "Synthesis of O-Phospholyrosine . . . Deportection Procedures", J. Org. Chem., vol. 55, pp. 4181-4187, 1990.
Chemical Abstracts, vol. 124, No. 1, p. 1004, 1996 (Abs. No. 9413).

Morelock et al., "Determination of Receptor . . . Phosphotyrosyl Peptides", J. of Med. Chem., vol. 38, pp. 1309-1318.

Shahripour et al., "Novel Phosphotyrosine . . . Domain", Bioorganic & Medicinal Chem. Letters, vol. 6, No. 11, pp. 1209-1214, 1996.

Rojas et al., "An Alternative . . . SH2 Domain", Biochemical and Biophysical Research Communications, vol. 234, pp. 675-680, 1997.

U.S. Appl. No. 09/937,150, filed Mar. 23, 2000, Burke, Jr. et al.

Jiang et al. "Hepatocyte growth factor/scatter factor, its molecular, cellular and clinical implications in cancer", Critical Reviews in Oncology/Hematology, 29:209-248 (1999).

* cited by examiner

*Primary Examiner*—Bruce R. Campell
*Assistant Examiner*—Andrew D. Kosar
(74) *Attorney, Agent, or Firm*—Leydig, Voit & Mayer, Ltd.

(57) ABSTRACT

Disclosed are methods of inhibiting cell motility, for example, by inhibiting the binding between an intracellular transducer and a receptor protein tyrosine kinase, and more particularly by inhibiting hepatocyte growth factor (HGF) induced cell motility. The present invention also provides a method of inhibiting angiogenesis. The methods of the present invention employ peptides such as phosphotyrosyl mimetics. The present invention further provides methods of preventing and/or treating diseases, disorders, states, or conditions such as cancer, particularly metastatic cancer comprising administering to a mammal of interest one or more peptides of the present invention. Also disclosed are methods of blocking HGF, VEGF, or bFGF-stimulated migration, cell proliferation, and formation of capillary-like structures

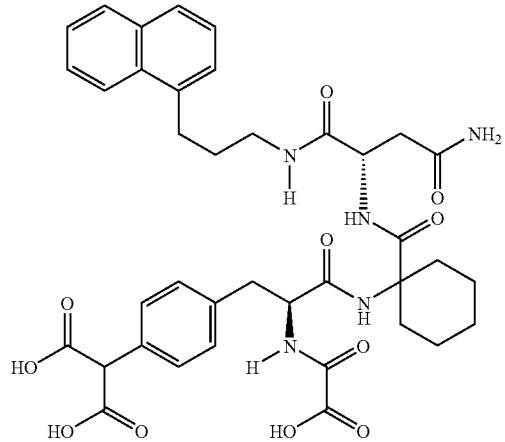

2

$C_{36}H_{43}N_5O_{11}$   MW745.8
106C-90

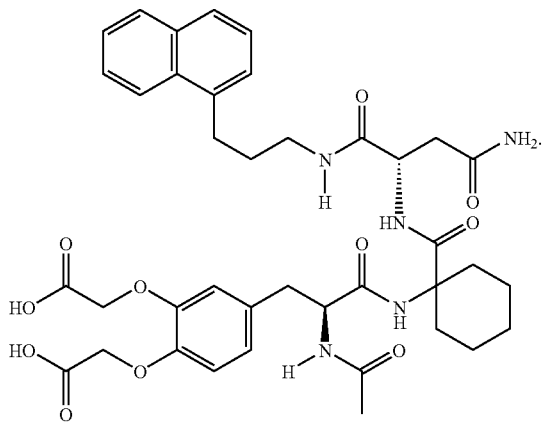

4

$C_{39}H_{47}N_5O_{11}$   MW7618
67N-35-B

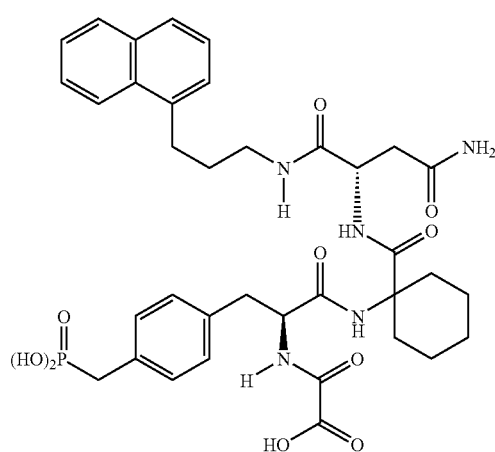

1

$C_{36}H_{44}N_5O_{10}P$   MW837.74
100C-126

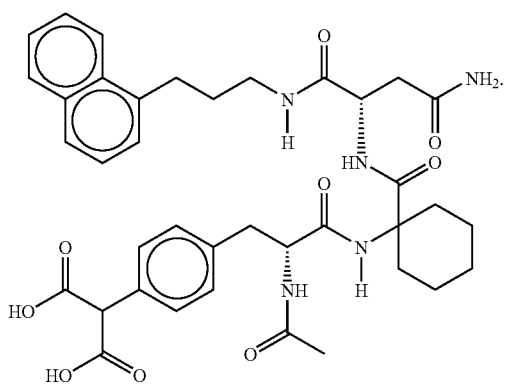

3

106-91
$C_{36}H_{45}N_5O_9$   mw.71580

36 Claims, 12 Drawing Sheets

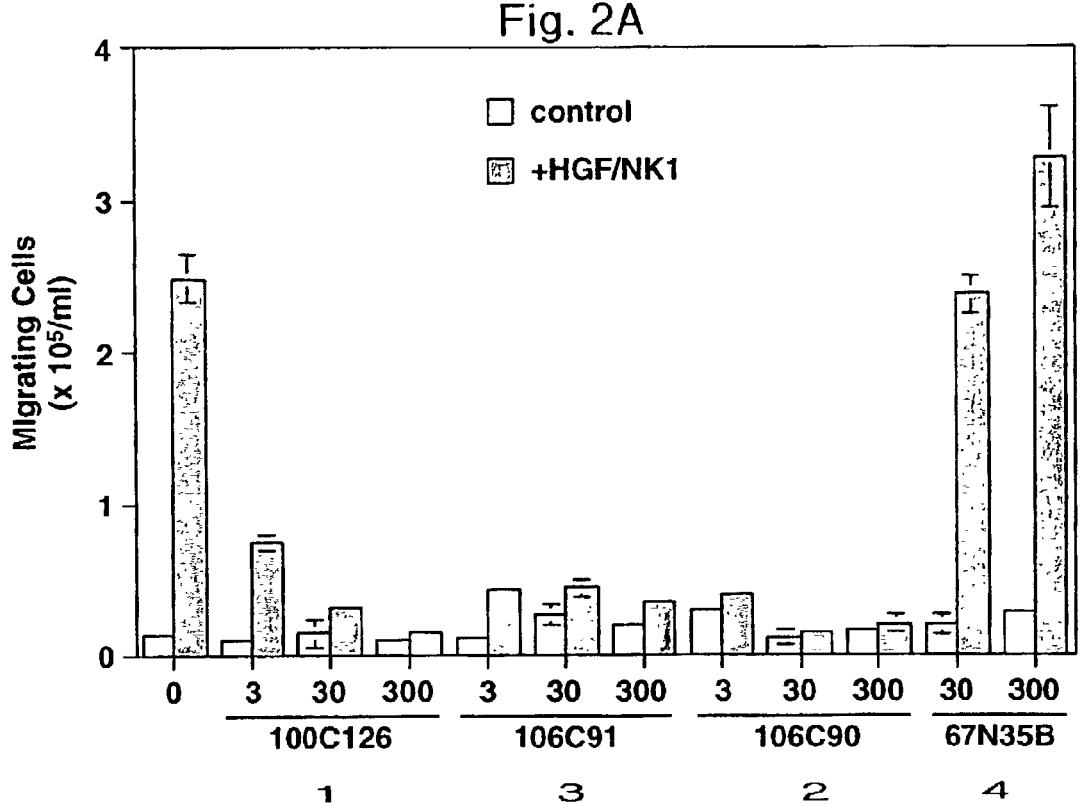
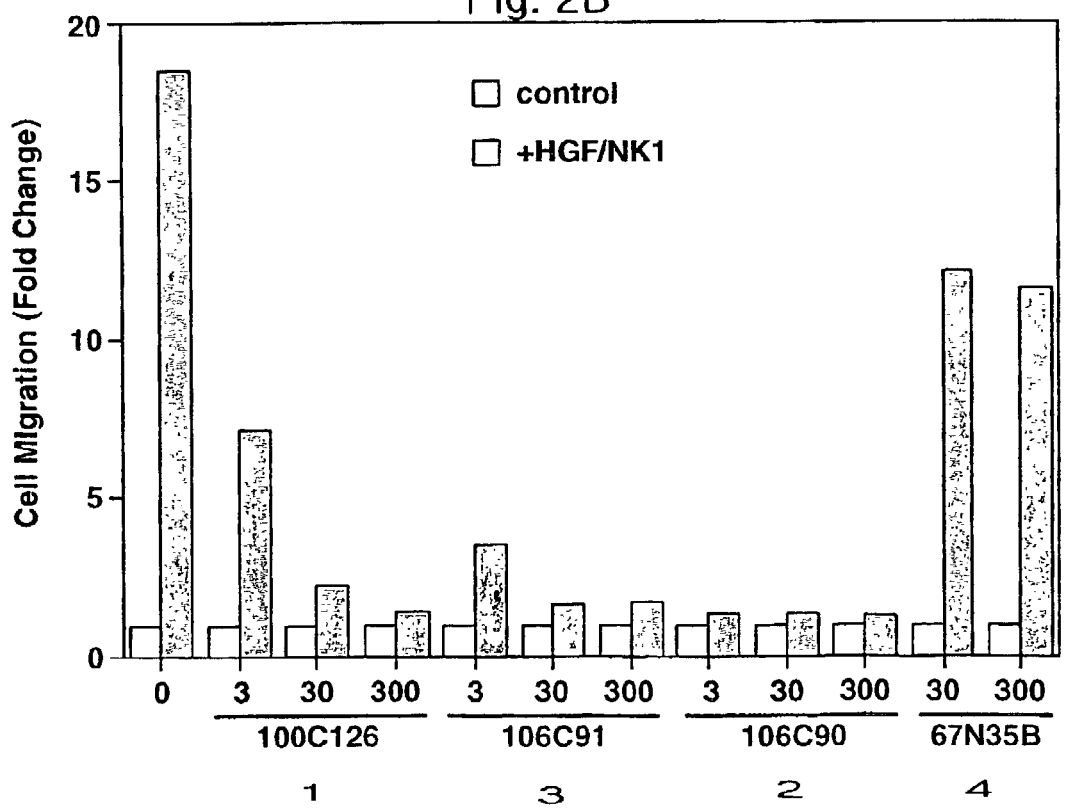

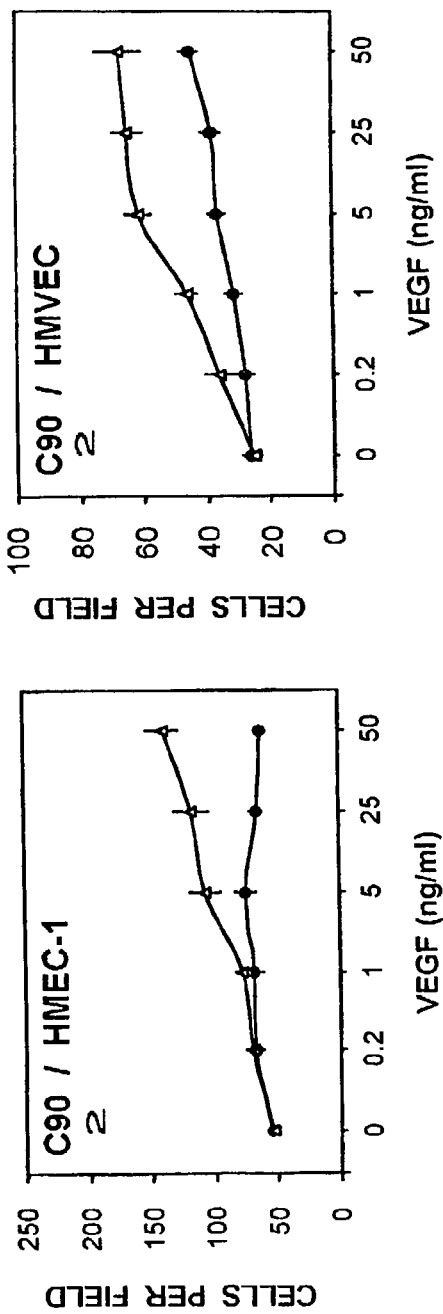
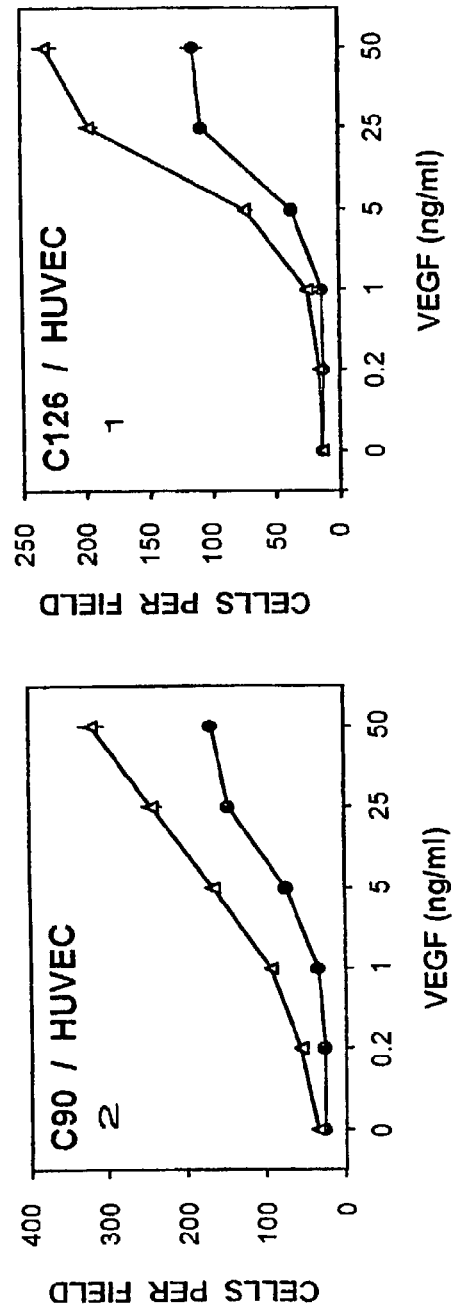

HUVEC

HMVEC

US 7,132,392 B1

INHIBITION OF CELL MOTILITY AND ANGIOGENESIS BY INHIBITORS OF GRB2-SH2-DOMAIN

CROSS REFERENCE TO RELATED PATENT APPLICATIONS

The present application claims the benefit of U.S. provisional patent application Ser. Nos. 60/160,899, filed Oct. 22, 1999 and 60/221,525, filed Jul. 28, 2000, which are incorporated by reference in their entireties.

FIELD OF THE INVENTION

The present invention in general relates to a method of inhibiting cell motility and angiogenesis and treating various diseases in a mammal, and particularly to a method of inhibiting cell motility and angiogenesis induced by the hepatocyte growth factor (HGF). The present invention also relates to a method of blocking HGF, VEGF and bFGF-stimulated cell migration, cell proliferation, and/or formation of capillary-like structure. The present invention also related to a method of treating cancer and cancer metastasis.

BACKGROUND OF THE INVENTION

The pharmaceutical industry is in search of a treatment and/or prophylaxis of proliferative diseases, disorders, or conditions such as cancers and cancer metastasis. These diseases, disorders, or conditions affect a large portion of the population, leading to suffering and possibly death.

Cancer is infrequently a localized disease as cancer cells detach from the primary tumor, translocate to distant sites, and grow as secondary colonies at the new anatomic locations leading to metastatic cancer. The motility of cancer cells is associated with cancer metastasis. The establishment of secondary colonies also is associated with the development of new blood vessels which supply the newly formed colony with blood and nutrients.

Development and progression of these diseases or disorders involve some form of intracellular signal transduction. Signal transduction is critical to normal cellular homeostasis and is the process of relaying extracellular messages, e.g., chemical messages in the form of growth factors, hormones and neurotransmitters, via receptors, e.g., cell-surface receptors, to the interior of the cell. Protein-tyrosine kinase enzymes play a central role in this biological function.

The above enzymes catalyze the phosphorylation of specific tyrosine residues to form tyrosine phosphorylated residues. The tyrosine-phosphorylated proteins are involved in a range of metabolic processes, from proliferation and growth to differentiation. An example of this class of enzymes is the receptor of the hepatocyte growth factor (HGF) (also known as the scatter factor (SF)), known as c-Met. HGF is a pleiotropic growth factor that, besides promoting cell survival and proliferation, has the ability to dissociate epithelial sheets and to stimulate cell motility. The dissociation of cell sheets and stimulation of cell motility is associated with the formation of new blood vessels, known as angiogenesis.

HGF stimulates mitogenesis, motogenesis, and morphogenesis in a wide range of cellular targets including epithelial and endothelial cells, hematopoietic cells, neurons, melanocytes, as well as hepatocytes. These pleiotropic effects play important roles during development and tissue regeneration. HGF signaling is also implicated in several human cancers including colon, breast, lung, thyroid, and renal carcinomas, several sarcomas, and glioblastoma. The ability of HGF to initiate a program of cell dissociation and increased cell motility coupled with increased protease production promotes aggressive cellular invasion and is linked to tumor metastasis.

Cell dissociation and increased cell motility, such as that induced by HGF, is also associated with angiogenesis. Angiogenesis is a complex and multi-step process that is essential for normal vascularization and wound repair. However, when the angiogenic process is not tightly regulated, persistent and uncontrolled neovascularization occurs, which contributes to tumor neovascularization and cancer metastasis.

HGF signals through its cell-surface receptor. Upon HGF binding, several tyrosine residues within the c-Met intracellular domain are phosphorylated, some of which mediate the binding of signaling proteins such as Grb2. Grb2 binding is involved in HGF-stimulated tubulogenesis, and is thought to link c-Met with small GTP-binding proteins such as Rho and Rac, which are required for HGF-stimulated cytoskeletal rearrangements and cell motility. Further, VEGF and bFGF are among the most potent regulators of angiogenesis, and share intracellular signaling mediators with a variety of angiogenesis signaling pathways. Folkman J., *EXS.* 79:1–8 (1997).

The foregoing indicates that there is a need for a method of inhibiting cell motility and angiogenesis. There further exists a need for inhibiting cell motility and angiogenesis induced by HGF. There further exists a need for inhibiting HGF, VEGF and bFGF-stimulated cell migration, cell proliferation, and/or formation of capillary-like structure. There further exists a need for a method of treating or preventing diseases such as cancers and cancer metastasis in mammals.

These advantages of the present invention will be apparent from the detailed description of the embodiments of the invention set forth below.

BRIEF SUMMARY OF THE INVENTION

Many of the foregoing needs have been fulfilled by the present invention that provides a method of inhibiting cellular motility. The present invention further provides a method for inhibiting angiogenesis in an animal. A method for inhibiting the binding of intracellular transducers to receptor protein tyrosine kinases is also provided by the present invention. The methods of the present invention employ peptides, e.g., phosphotyrosine mimetics, to inhibit cell motility and angiogenesis. The present invention further provides methods of preventing and/or treating diseases, disorders, states, or conditions such as cancer, particularly metastatic cancer. An advantage of the methods of the present invention is that the peptides are free of cytotoxicity.

The present invention provides a method for blocking HGF-stimulated cellular matrix invasion, a method for blocking HGF-stimulated branching tubulogenesis, a method for blocking HGF, VEGF, or bFGF-stimulated migration, a method for blocking HGF, VEGF, or bFGF-stimulated cell proliferation, and a method for blocking HGF, VEGF, or bFGF-stimulated formation of capillary structures. The phosphotyrosine mimetic peptides disclosed herein block HGF-stimulated matrix invasion by cultured epithelial cells or vascular endothelial cells. The peptides also block HGF-stimulated branching tubulogenesis by cultured epithelial cells or vascular endothelial cells, e.g., those grown in a three-dimensional extracellular matrix. The peptides also block HGF-, VEGF- and bFGF-stimulated migration by vascular endothelial cells, e.g., those cultured in modified Boyden chambers. The peptides also block HGF-, VEGF- and bFGF-stimulated vascular endothelial cell proliferation, e.g., in vitro. The peptides further block HGF-, VEGF- and bFGF-stimulated formation of capillary-like structures by vascular endothelial cells, e.g., those cultured on a reconstituted extracellular matrix (Matrigel) in vitro. The peptides block in vivo angiogenesis also, as shown, e.g., by a chick allantoid membrane assay.

While the invention has been described and disclosed below in connection with certain embodiments and procedures, it is not intended to limit the invention to those specific embodiments. Rather it is intended to cover all such alternative embodiments and modifications as fall within the spirit and scope of the invention.

BRIEF DESCRIPTION OF THE DRAWINGS

FIG. 1 also depicts the structural formula of the control peptide 4.

FIGS. 2A and 2B depict the effect of peptides 1–3 on the migration of 32D/c-Met cells. In FIGS. 2A and 2B, the x-axis represents the concentrations of the peptides in nM and unfilled bars represent the migration of cells in the absence of HGF/NK1, and the shaded bars represent the migration of cells in the presence of HGF/NK1 (1 microgram per ml, final concentration). In FIG. 2A, the Y-axis represents the number of migrating cells. In FIG. 2B, the Y-axis represents the fold or change in cell migration. Also included in FIGS. 2A and 2B are results obtained on peptide 4.

In FIGS. 3A and 3B, the X-axis represents the concentrations of the peptides in nM; the unfilled bars represent the migration of cells in the absence of HGF/NK1, and the shaded bars represent the migration of cells in the presence of HGF/NK1 (300 nanograms per ml, final concentration). In FIG. 3A, the Y-axis represents the number of migrating cells. In FIG. 3B, the Y-axis represents the fold or change in cell migration. Also included in FIG. 3A are the results obtained on peptide 4.

In FIGS. 6A–B, unfilled bars represent the migration of cells in the absence of HGF, while filled bars represent the migration of cells in the presence of HGF. The gray shaded bars of FIG. 6B represent the migration of cells in the presence of bFGF.

In FIGS. 8A–B, the reported values are mean number of cells per optical field. Error bars indicate standard error of the mean (s.e.m.) of values from triplicate wells per experimental condition; where no error bars are visible, the error is too small to be shown.

FIG. 9A depicts the effect of peptide 2 on VEGF-induced cell migration by HMEC-1 cells, FIG. 9B depicts the effect of peptide 2 on VEGF-induced migration by HMVE cells, FIG. 9C depicts the effect of peptide 2 on VEGF-induced cell migration by HUVE cells, and FIG. 9D depicts the effect of peptide 1 on VEGF-induced cell migration by HUVE cells.

DETAILED DESCRIPTION OF EMBODIMENTS

Figure 1:
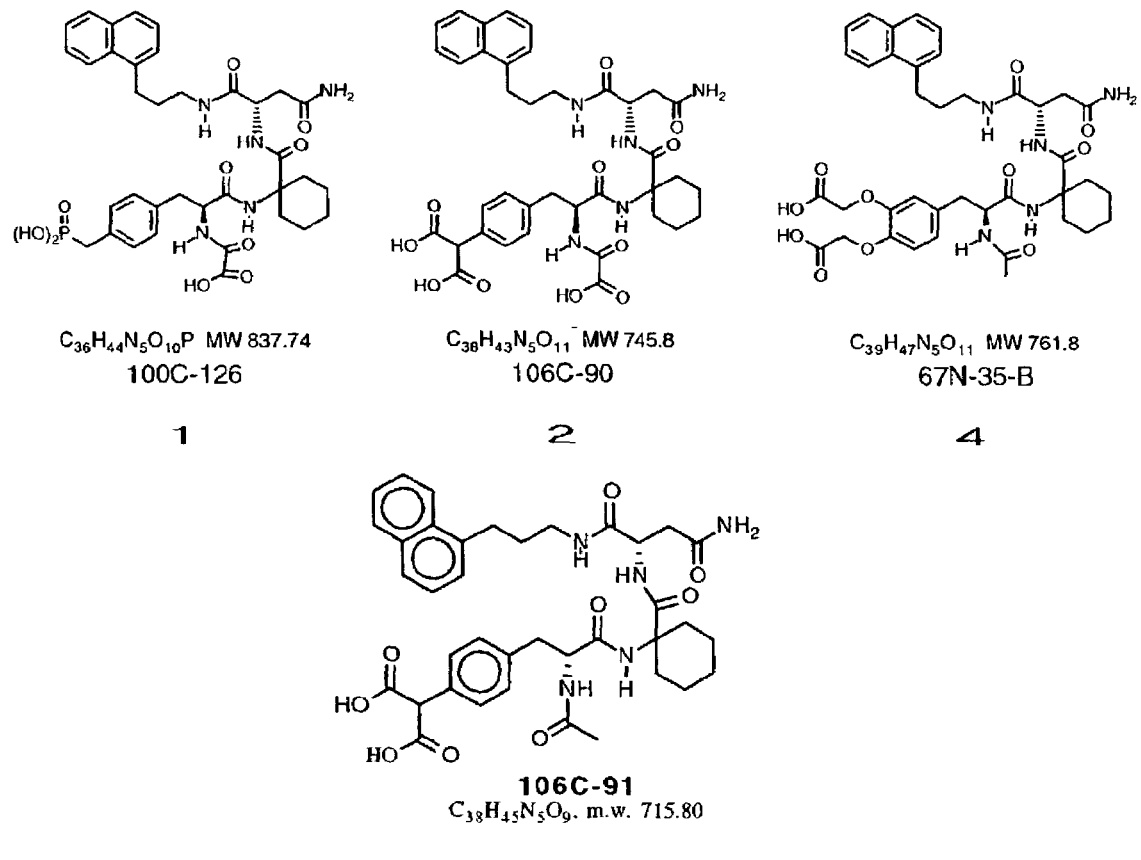
FIG. 1 depicts the structural formulas of peptides 1–3 that can find use in the method in accordance with embodiments of the present invention.

The present invention provides a method for inhibiting cell motility. The present invention also provides a method for inhibiting angiogenesis in an animal. The present invention further provides a method for preventing or treating a variety of diseases, disorders, states or conditions in a mammal, particularly in a human.

The present invention provides a method of inhibiting cell motility in a mammal comprising administering to the mammal a peptide having cell signal inhibiting activity and cell motility inhibiting activity. Advantageously, the peptide is free or substantially free of cytotoxicity.

The present invention contemplates to retard or reduce the movement of cells. A number of factors, forces, and/or mechanisms are involved in the movement of cells from one location to another. The method of the present invention is not limited to inhibiting or interfering with one particular factor, force, or mechanism that is involved in the cell movement.

The process of cell movement begins with extension of the cell membrane, the push forward of cytosol (the inner material of the cell), and retraction of the rear of the cell. As the cell membrane initially is propelled forward, an attachment forms between the membrane and the substratum, thereby anchoring the "head" of the cell. Some believe that the cytosol is pushed forward by restructuring of the cytoskeletal network within the cell, although the exact mechanism is unknown. The final step involves the detachment of the "tail" of the cell from the substratum.

It is believed that growth factors activate a signal transduction pathway involving G-proteins, which promote cytoskeletal changes including actin polymerization. External factors promote cell motility by binding to a cell surface receptor and activating a signal transduction pathway, e.g., one involving G-proteins. The signal transduction pathway, in turn, promotes reorganization of the cytoskeleton. A variety of extracellular factors influence cell motility. The movement of a cell following soluble molecules along a concentration gradient is called chemotaxis. Intracellular calcium may play a role in the ability of a cell to recognize concentration gradients. Hormones such as insulin, cytokines, and specific peptide fragments of the extracellular matrix have been identified which stimulate tumor cell motility and chemotaxis.

Aside from instigating cell motility, growth factors stimulate neovascularization, which involves, in part, cell movement. Angiogenesis begins with proteolytic enzyme-mediated breakdown of the basement membrane of a blood vessel. It is believed that breakdown of the basement membrane is regulated by angiogenic factors, such as fibroblast growth factor. Endothelial cells migrate to the area of degradation and invade the surrounding extracellular matrix. Invading endothelial cells proliferate, forming an elongated column of cells. A lumen forms within the solid cell column, thereby forming a vessel, which eventually connects with an existing blood vessel forming a capillary loop (Fotsis et al., J. Nutr., 125: 790S–797S (1995)).

The present invention provides a method for inhibiting angiogenesis in an animal, e.g., a mammal. The method comprises administering to the animal, e.g., mammal, a peptide having cell signal inhibiting activity and cell motility inhibiting activity, wherein the peptide is substantially free of cytotoxicity. Preferably, the peptide affects multiple aspects of the angiogenic process to effectively therapeutically or prophylactically treat angiogenesis. For example, in addition to inhibiting cell signaling and cell motility, the peptide preferably inhibits invasion of epithelial and/or endothelial cells into the extracellular matrix.

In one embodiment, the present invention provides a method of inhibiting cell motility and angiogenesis induced by the hepatocyte growth factor (HGF), particularly the motility derived from a biological response mediated by its cell surface receptor, the c-Met proto-oncogene product, a transmembrane tyrosine kinase. Upon HGF binding, several tyrosine residues within the c-Met intracellular domain are phosphorylated. Some of the phosphorylated domains mediate binding with various signaling proteins, e.g., the Grb2 protein, the p85 subunit of phosphoinositide 3-kinase (PI3K), phospholipase C-gamma, Shc, and Gab1.

Preferably, the peptide of the present inventive method is a peptide that inhibits Grb2 SH2 domain binding. In this regard, it is imperative to cellular function that a transducer protein accurately identify activated cellular receptors. Most often, recognition specificity stems from the ability of the transducer protein to recognize a phosphotyrosine surrounded by a specific amino acid sequence. The recognition motif for Grb2 is pYXN wherein pY is phospho-Tyr, X is any amino acid, and N is Asn. Therefore, the peptide of the present inventive method, in certain embodiments recognizes and binds a pYXN motif. The method of the present invention is directed to inhibiting cell motility induced or mediated by signaling due to one or more of the above HGF bindings, preferably the binding of HGF c-Met receptor with the Grb2 protein.

The peptide employed in certain embodiments of the present invention has the formula I

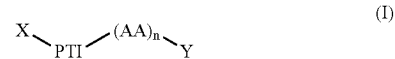

wherein n is 0 to 15, X is a group that modifies an amino group to an amide, PTI is a bivalent radical of tyrosine, a bivalent radical of phosphotyrosine, or of a phosphotyrosine mimetic; AA stands for a bivalent radical of a natural or unnatural amino acid; and Y is a secondary amino group; or a salt thereof.

PTI in formula I above is a bivalent radical of phosphotyrosine or of a phosphotyrosine mimetic. In a preferred embodiment, n in formula I is 1–4. In certain embodiments, n is 1–4 and PTI is a bivalent radical of tyrosine or a bivalent radical of phosphotyrosine or of a phosphotyrosine mimetic in the form of a bivalent radical of an amino acid selected from the group consisting of phosphonomethyl-phenylalanine, phosphono-α-fluoro)methyl-phenylalanine, phosphono-(α,α-difluoro)methyl-phenylalanine, phosphono-(α-hydroxy)methyl-phenylalanine, O-sulfo-tyrosine, dicarboxymethoxy-phenylalanine, aspartic acid, glutamic acid, phosphoserine and phosphothreonine, each of which can be present in the (D,L)-, D- or L-form;

-(AA)$_n$— is a bivalent radical of a tripeptide of the formula -(AA$^1$)-(AA$^2$)-(AA$^3$)-, wherein -(AA$^1$)- is selected from the group consisting of -Ile-, -Ac$_5$c-, -Ac$_6$c-, -Asp-, -Gly-, -Phe-, -Ac$_7$c-, -Nbo-, -Met-, -Pro-, -β-Ala-, -Gin-, -Glu-, -DHph-, -HPh- and -tLe-; -(AA$^2$)- is selected from the group consisting of -Asn-, -β-Ala-, -Gly-, -Ile-, and -Gin-; and -(AA$^3$)- is selected from the group consisting of -Val-, -β-Ala-, -Gly-, -Gin-, -Asp- and Ac$_5$c-; a bivalent radical of a dipeptide of the formula -(AA$^1$)-(AA$^2$)- wherein -(AA$^1$)- and -(AA$^2$)- are as recited above;

or a bivalent radical of an amino acid selected from the amino acids mentioned above; and Y is a monosubstituted amino selected from the group consisting of lower alkylamino, octylamino, halonaphthyloxy-lower alkylamino, naphthyloxy-lower alkylamino, phenyl-lower alkylamino, di-phenyl-lower alkylamino, (mono- or di-halo-phenyl)-lower alkylamino, naphthalenyl-lower alkylamino, hydroxy-naphthalenyl-lower alkylamino, phenanthrenyl-lower alkylamino; cycloalkylamino; and cycloalkyl-lower alkylamino;

or a salt thereof.

In some other embodiments of the present invention n is 1 to 4; PTI is a bivalent radical of phosphotyrosine or of a phosphotyrosine mimetic in the form of a bivalent radical of an amino acid selected from the group consisting of phosphonomethyl-phenylalanine, phosphono-α-fluoro)methyl-phenylalanine, phosphono-(α,α-difluoro)methyl-phenylalanine, phosphono-α-hydroxy)-methyl-phenylalanine, O-sulfo-tyrosine, dicarboxymethoxy-phenylalanine, aspartic acid, glutamic acid, phosphoserine and phosphothreonine, each of which is present in the (D,L)-, D- or L-form;

-(AA)$_n$- is a bivalent radical of a tripeptide of the formula -(AA$^1$)-(AA$^2$)-(AA$^3$)- wherein -(AA)- is selected from the group consisting of -Ile-, -Ac$_6$c—, -Asp-, -Gly- and -Phe-, -(AA$^2$)- is selected from the group consisting of -Asn-, -β-Ala- and -Gly-; and -(AA³)- is selected from the group consisting of -Val-, -β-Ala-, -Gly-, -Gln-, -Asp- and -Ac₅c-;

a bivalent radical of a dipeptide of the formula -(M¹)-(AA²)- wherein -(AA¹)- is -Ile- or -Ac₆c- and -(AA²)- is -Asn- or -β-Ala-;

or a bivalent radical of the amino acid selected from the amino acids mentioned above; and Y is a mono substituted amino group having a substituent selected from the group consisting of lower alkyl and aryl-lower alkyl;

or a salt thereof. In certain other embodiments of the present invention, n is 1 to 4; PTI is a bivalent radical of tyrosine or a bivalent radical of phosphotyrosine mimetic in the form of a bivalent radical of an amino acid selected from the group consisting of phosphonomethyl-phenylalanine, phosphono-(α-fluoro)methyl-phenylalanine, phosphono-(α,α-difluoro) methyl-phenylalanine, phosphono-α-hydroxy)methyl-phenylalanine, O-sulfo-tyrosine, dicarboxymethoxy-phenylalanine, aspartic acid, glutamic acid, phosphoserine and phosphothreonine, each of which can be present in the (D,L)-, D- or the L-form;

-(AA)ₙ— is a bivalent radical of a tripeptide of the formula -(AA¹)-(AA²)-(AA³)- wherein -(M¹)- is selected from the group consisting of -Ile-, -Ac₅c-, Ac₆c-, -Asp-, -Gly-, -Phe-, -Ac₇c-, -Nbo-, -Met-, -Pro-, -β-Ala-, -Gln-, -Glu-, -DHph-, -HPh- and -tLe-; -(AA²)- is selected from the group consisting of -Asn-, -β-Ala-, -Gly-, -Ile-, and -Gln-; and -(AA³)- is selected from the group consisting of -Val-, -β-Ala, -Gly-, -Gln-, -Asp- and -Ac₅c-; or a bivalent radical of an amino acid selected from the amino acids mentioned above; and Y is a monosubstituted amino selected from the group consisting of lower alkylamino, octylamino, halonaphthyloxy-lower alkylamino, naphthyloxy-lower alkylamino, phenyl-lower alkylamino, di-phenyl-lower alkylamino, (mono- or di-halo-phenyl)-lower alkylamino, naphthalenyl-lower alkylamino, hydroxy-naphthalenyl-lower alkylamino or phenanthrenyl-lower alkylamino, cycloalkylamino, and cycloalkyl-lower alkylamino; or a salt thereof.

In formula I, X is a moiety attached to the nitrogen of PTI and is selected from the group consisting of $C_1$–$C_6$ alkylcarbonyl, oxalyl, $C_1$–$C_6$ alkylaminooxalyl, arylaminooxalyl, aryl $C_1$–$C_6$ alkylaminooxalyl, $C_1$–$C_6$ alkoxyoxalyl, carboxy $C_1$–$C_6$ alkyl carbonyl, heterocyclyl carbonyl, heterocyclyl $C_1$–$C_6$ alkyl carbonyl, aryl $C_1$–$C_6$ alkyl heterocyclyl $C_1$–$C_6$ alkyl carbonyl, aryloxycarbonyl, and aryl $C_1$–$C_6$ alkoxycarbonyl. In a preferred embodiment, X is oxalyl. Particular examples of peptides include oxalyl-Pmp-Ile-Asn-NH-(3-naphthalen-1-yl-propyl), oxalyl-Pmp-Ile-Asn-NH-(3-(2-hydroxy-naphthalen-1-yl)-propyl), oxalyl-Pmp-Ile-Asn-NH-(3-naphthalen-2-yl-propyl), and oxalyl-Pmp-Ac₆c-Asn-NH-(3-naphthalen-1-yl-propyl) wherein "Pmp" stands for phosphonomethyl phenylalanine.

In yet other embodiments, the peptide has the formula I, wherein PTI is a phenylalanyl radical having a phenyl ring, an amine end, and a carboxyl end, the phenyl ring having one or more substituents selected from the group consisting of hydroxyl, carboxyl, formyl, carboxyalkyl, carboxyalkyloxy, dicarboxyalkyl, dicarboxyalkyloxy, dicarboxyhaloalkyl, dicarboxyhaloalkyloxy, and phosphonoalkyl, phosphonohaloalkyl, wherein the alkyl portion of the substituents may be unsubstituted or substituted with a substituent selected from the group consisting of halo, hydroxy, carboxyl, amino, aminoalkyl, alkyl, alkoxy, and keto;

X is a moiety attached to the nitrogen of PTI and is selected from the group consisting of alkylcarbonyl, oxalyl, alkylaminooxalyl, arylaminooxalyl, arylalkylaminooxalyl, alkoxyoxalyl, carboxyalkyl carbonyl, heterocyclyl carbonyl, heterocyclylalkyl carbonyl, arylalkyl heterocyclylalkyl carbonyl, aryloxycarbonyl, and arylalkoxycarbonyl, wherein the aryl and alkyl portions of the substituents may be unsubstituted or substituted with a substituent selected from the group consisting of halo, hydroxy, carboxyl, amino, aminoalkyl, alkyl, alkoxy, and keto; and the heterocyclyl portion of Y contains at least 4 hetero atoms selected from the group consisting of O, N, and S;

AA is an amino acid, the amine end of which is attached to the carboxyl end of PTI; and Y is an arylalkylamino or arylheterocyclyl alkylamino;

or a salt thereof.

Certain other embodiments of the present invention employ peptides wherein PTI is a phenylalanyl radical having a phenyl ring, an amine end, and a carboxyl end, the phenyl ring having one or more substituents selected from the group consisting of hydroxyl, carboxyl, formyl, carboxy $C_1$–$C_6$ alkyl, carboxy $C_1$–$C_6$ alkyloxy, dicarboxy $C_1$–$C_6$ alkyl, dicarboxy $C_1$–$C_6$ alkyloxy, dicarboxyhalo $C_1$–$C_6$ alkyl, dicarboxyhalo $C_1$–$C_6$ alkyloxy, and phosphono $C_1$–$C_6$ alkyl, phosphonohalo $C_1$–$C_6$ alkyl, wherein the alkyl portion of the substituents may be unsubstituted or substituted with a substituent selected from the group consisting of halo, hydroxy, carboxyl, amino, aminoalkyl, $C_1$–$C_6$ alkyl, $C_1$–$C_6$ alkoxy, and keto;

X is a moiety attached to the nitrogen of PTI and is selected from the group consisting of $C_1$–$C_6$ alkylcarbonyl, oxalyl, $C_1$–$C_6$ alkylaminooxalyl, arylaminooxalyl, aryl $C_1$–$C_6$ alkylaminooxalyl, $C_1$–$C_6$ alkoxyoxalyl, carboxy $C_1$–$C_6$ alkyl carbonyl, heterocyclyl carbonyl, heterocyclyl $C_1$–$C_6$ alkyl carbonyl, aryl $C_1$–$C_6$ alkyl heterocyclyl $C_1$–$C_6$ alkyl carbonyl, aryloxycarbonyl, and aryl $C_1$–$C_6$ alkoxycarbonyl, wherein the aryl and alkyl portions of the substituents may be unsubstituted or substituted with a substituent selected from the group consisting of halo, hydroxy, carboxyl, amino, amino $C_1$–$C_6$ alkyl, $C_1$–$C_6$ alkyl, $C_1$–$C_6$ alkoxy, and keto; and the heterocyclyl portion of Y contains at least 4 hetero atoms selected from the group consisting of O, N, and S;

AA is an amino acid, the amine end of which is attached to the carboxyl end of PTI; and Y is an aryl $C_1$–$C_6$ alkylamino or arylheterocyclyl $C_1$–$C_6$ alkylamino; or a salt thereof.

In any of the above embodiments, substituents can be present at any suitable position on the phenyl ring of phenyl alanine, preferably at the position para to the benzylic methylene group.

The peptides of formula I that can be employed in the method of the present invention include peptides wherein PTI is of the formula II:

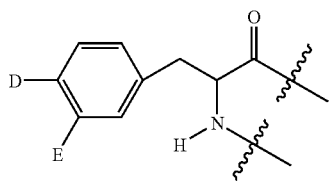
(II)

wherein D has the formula III, IV, or V:

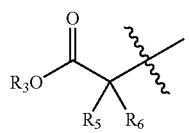
(III)

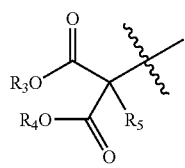
(IV)

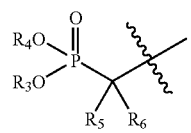
(V)

wherein $R_3$ and $R_4$ may be the same or different and are selected from the group consisting of hydrogen, $C_1$–$C_6$ alkyl, aryl, aryl $C_1$–$C_6$ alkyl, $C_1$–$C_6$ alkaryl, and heteroaryl; and $R_5$ and $R_6$ may be the same or different and are selected from the group consisting of hydrogen, halo, hydroxy, amino, and $C_1$–$C_6$ alkoxy; and E is selected from the group consisting of hydrogen, $C_1$–$C_6$ alkyl, $C_1$–$C_6$ alkylcarbonyl, carboxyl, and $C_1$–$C_6$ alkylcarbonyl $C_1$–$C_6$ alkyl.

A particular example of Y is aryl $C_1$–$C_6$ alkylamino. In embodiments of peptides used in the present inventive method, the aryl portion of Y has the formula:

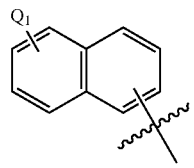

wherein $Q_1$ is hydrogen or a substituent selected from the group consisting of hydroxyl, halo, $C_1$–$C_6$ alkyl, $C_1$–$C_6$ alkoxy, amino, and $C_1$–$C_6$ acylamino. The heteroaryl portion in certain embodiments of Y has the formula:

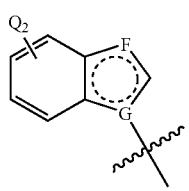

wherein $Q_2$ is hydrogen or a substituent selected from the group consisting of hydroxyl, halo, $C_1$–$C_6$ alkyl, $C_1$–$C_6$ alkoxy, amino, and $C_1$–$C_6$ acylamino, and F and G are independently selected from the group consisting of C, N, O, and S.

Although any suitable X can be present in the peptide, X is preferably selected from the group consisting of acetyl, oxalyl, $C_1$–$C_6$ alkylaminooxalyl, arylaminooxalyl, aryl $C_1$–$C_6$ alkylaminooxalyl, $C_1$–$C_6$ alkoxyoxalyl, carboxymethylcarbonyl, tetrazolylcarbonyl, tetrazolylmethylcarbonyl, aminophenylmethoxycarbonyl, amino naphthyloxycarbonyl, and methoxyphenylmethyl tetrazolylmethylcarbonyl, and more preferably X is oxalyl.

In certain peptides according to preferred embodiments of the present invention, n is 1–3.

Particular examples of peptides include (N-oxalyl-4-malonyl)-Phe-Ac$_6$c-Asn-NH-(3-naphthalen-1-yl-propyl), peptide 2, and (N-acetyl-4-malonyl)-Phe-Ac$_6$c-Asn-NH-(3-naphthalen-1-yl-propyl), peptide 3.

Peptides having cell signaling inhibitory activity and cell motility inhibiting activity, such as Grb2-SH2 domain mimetic peptides, are particularly useful in inhibiting neovascularization. As demonstrated in Example 2, peptides having cell signaling inhibitory activity and cell motility inhibiting activity, such as the Grb2-SH2 domain mimetic peptides described herein, inhibit endothelial cell and epithelial cell invasion of matrices and the formation of cell cords. The assays used in Example 2 mirror the angiogenic process in vivo. For instance, Matrigel is comprised of reconstituted basement membrane proteins. Cells that invade the Matrigel matrix form elongated cell cords, which eventually form interconnections (Baatout, *Anticancer Research*, 17: 451–456 (1997)). Invasion of the extracellular matrix and the formation of columns of cells therein are important processes associated with angiogenesis in vivo.

In accordance with certain embodiments, the method of the present invention is contemplated for use in preventing or treating various diseases, states, disorders, or conditions, particularly cancer. Examples of diseases, states, disorders, or conditions that are contemplated include cancers such colon cancer, breast cancer, lung cancer, thyroid cancer, and renal cancer, sarcoma, glioblastoma, and cancer or tumor metastasis. In accordance with some embodiments, the method of the present invention can be carried out in vitro or in vivo.

The peptides of the present invention can be prepared by methods known to those skilled in the art. Thus, the peptides can be synthesized by the solution phase or solid phase synthetic techniques. See, e.g., Yao et al., *J. Med. Chem.*, 42, 25–35 (1999); Ye et al., *J. Med. Chem.*, 38, 4270–4275 (1995); Burke, Jr. et al., *Biochemistry*, 33, 6490–6494 (1994); Smyth et al., *Tetr. Lett.*, 35, 551–554 (1994); Burke, Jr. et al., *J. Org. Chem.*, 58, 1336–1340 (1993); and Burke, Jr. et al., *Tetr. Lett.*, 34, 4125–4128 (1993).

For example, the peptides having a phosphonomethyl group on the phenyl ring of phenyl alanine, such as peptide 1, can be prepared by the procedures described in U.S. patent application Ser. No. 09/236,160, filed Jan. 22, 1999, particularly in Schemes 1–4 and the Experimental section. The disclosure of this application is incorporated herein in its entirety by reference. Thus, for example, peptide 1 can be prepared by the reaction of t-butyl oxalyl chloride with a naphthylpropylamido tripeptide containing a phenylalanine terminal residue whose amino nitrogen is protected by a protecting group such as F-moc.

The naphthylpropylamido tripeptide can be prepared by reacting naphthylpropylamine with N-Boc-L-Asn-N-hydroxysuccinimide ester. The resulting naphthylpropylamido monopeptide can be further reacted with a N-protected aminocyclohexane carboxylic acid to obtain a naphthylpropylamido dipeptide. The dipeptide can then be reacted with a phosphonomethyl phenyl alanine to obtain the naphthylpropylamido tripeptide. The naphthylpropylamine can be prepared starting from naphthaldehyde.

As a further example, peptides having a malonyl group on the phenyl ring of phenyl alanine, such as peptide 2, can be prepared by the by the procedures described in the provisional application Ser. No. 60/126,047, filed Mar. 23, 1999, particularly in FIGS. 1, 4–5, and 7 and Examples 1–2. The disclosure of this application is incorporated herein in its entirety by reference. Thus, for example, peptide 2 can be prepared as follows. A naphthylpropylamido dipeptide can be prepared as above. The dipeptide can then be reacted with a di-t-butoxy-malonylated phenyl alanine whose α-amino group has been N-protected. The resulting di-t-butoxymalonylated tripeptide can be reacted with t-butoxy oxalyl chloride. The t-butoxy groups can then be cleaved off the resulting tripeptide to obtain peptide 2.

The di-t-butoxy-malonylated phenyl alanine whose α-amino group has been N-protected can be prepared starting from p-iodotoluene by reaction with di-t-butyl malonate. The resulting malonylated toluene derivative can be halogenated, e.g., brominated, at the methyl group to provide an α-halotoluene malonate derivative. The latter derivative can be reacted with a benzyl-6-oxo-2,3-diphenyl-4-morpholine, and the resulting morpholino derivative can be reduced with palladium and hydrogen to provide a malonylated phenyl alanine. The α-amino group of this phenyl alanine can be N-protected by known N-protecting groups such as F-moc.

In the practice of the method of the present invention, the peptides can be administered as a pharmaceutical composition comprising a pharmaceutically acceptable carrier and an effective (e.g., therapeutically or prophylactically effective) amount of at least one of the peptides. The pharmaceutically acceptable (e.g., pharmacologically acceptable) carriers described herein, for example, vehicles, adjuvants, excipients, or diluents, are well-known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can comprise (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The peptides, alone or in combination with other suitable components, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants. The quantity of surfactant in such formulations typically ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The peptides or derivatives thereof may also be made into injectable formulations. The requirements for effective pharmaceutical carriers for injectable compositions are well known to those of ordinary skill in the art. See, e.g., *Pharmaceutics and Pharmacy Practice*, J.B. Lippincott Co., Philadelphia, Pa., Banker and Chalmers, eds., pages 238–250 (1982), and *ASHP Handbook on Injectable Drugs*, Toissel, 4th ed., pages 622–630 (1986).

Additionally, the peptides of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day if desired. In proper doses and with suitable administration of certain compounds, the present invention provides for a wide range of responses. Typically the dosages range from about 0.001 to about 1000 mg/kg body weight of the animal being treated/day. Preferred dosages range from about 0.01 to about 10 mg/kg body weight/day, and further preferred dosages range from about 0.01 to about 1 mg/kg body weight/day.

The effects of the methods of the present invention can be determined by any suitable methods, such as methods known to those skilled in the art. For example, the present invention provides a method of inhibiting, in whole or in part, angiogenesis. The ordinarily skilled artisan has the ability to detect inhibition of angiogenesis using a variety of methods, such as, for example, fluorescein angiography, scanning electron microscopy, and generation of vascular casts. In addition, several animal models of angiogenesis exist including, but not limited to, the mouse ear model of neovascularization, models of ocular neovascularization in rabbits, and the rat hindlimb ischemia model of neovascularization. In the treatment of cancer, the change in tumor size can be measured, e.g., by imaging techniques, at suitable intervals during the treatment period as well as after the treatment is discontinued. Alternatively, biological fluid samples, e.g., blood samples can be drawn at predetermined intervals to determine the concentration of cancer cells therein. Biopsy can be carried out to determine the characteristics of tumor cells. The peptides of the present invention are contemplated for use in the prevention of diseases. Thus, a disease, e.g., metastasis of cancer, is contemplated to be prevented in whole or in part.

The peptides of the present invention have the advantage that they are stable to or in presence of enzymes encountered during in vivo use. The peptides can find use in in vitro and in vivo applications. For example, they can find use as molecular probes as well as in assays to identify, isolate, and/or quantitate receptor or binding sites in a cell or tissue. The peptides also can find use in vivo for studying the efficacy in the treatment of various diseases or conditions involving SH2 domains.

The present invention further provides a method for inhibiting the binding between an intracellular transducer and a receptor protein tyrosine kinase that influences cell motility comprising contacting the receptor with a peptide of the present invention, or an ester or ether derivative thereof. An example of an intracellular transducer is one that includes one or more SH2 domains, preferably the Grb2 transducer. An example of a receptor protein tyrosine kinase is the HGF factor, particularly the HGF/c-Met receptor.

The peptides of the present invention interact with intracellular signal transducers, thus interfering in the pathways leading to cell proliferation and movement. These biological effects can be utilized to inhibit growth of neoplastic cells, inhibit angiogenesis, and to prevent metastatic spreading. The present invention provides a method for preventing or treating a disease, condition, or state in a mammal that is mediated by the binding of an intracellular transducer to a receptor protein tyrosine kinase comprising administering to the mammal a peptide of the present invention.

The peptides of the present invention can be used to prevent and/or treat a disease, disorder, state, or condition such as cancer. Examples of cancers that may be prevented or treated include, but are not limited to, colon cancer, breast cancer, lung cancer, thyroid cancer, and renal cancer. Further examples of disease, disorder, state, or condition that can be prevented or treated include sarcoma, lymphoma, melanoma, leukemia, glioblastoma, and tumor metastasis.

The present invention further provides a method for inhibiting the binding of an intracellular transducer to a receptor protein tyrosine kinase comprising contacting (a) a sample containing the receptor protein tyrosine kinase, (b) the intracellular transducer, and (c) the peptide of the present invention, under conditions wherein, in the absence of the peptide, the receptor protein tyrosine kinase binds to the intracellular transducer; wherein the contacting results in the inhibition of binding of the intracellular transducer to the receptor protein tyrosine kinase.

The present invention further provides a method for detecting the inhibition of binding of an intracellular transducer to a receptor protein tyrosine kinase comprising (a)

contacting a sample containing the receptor protein tyrosine kinase with the intracellular transducer, and separately, in the presence and absence of the peptide of the present invention or a derivative thereof, under conditions that allow for binding of the receptor protein tyrosine kinase to the intracellular transducer in the absence of the peptide; (b) detecting whether binding has occurred between the receptor protein tyrosine kinase and the intracellular transducer; and (c) comparing relative binding levels of the receptor protein tyrosine kinase to the intracellular transducer in the presence and absence of the peptide; wherein the detection of decreased binding in the presence of the peptide indicates inhibition of binding.

The present invention further provides a method for determining the presence of a Grb2 protein in a material comprising (a) exposing a sample of the material to a Grb2 binding compound and obtaining a first binding result; (b) exposing another sample of the material to a peptide of the present invention, or a derivative thereof, and obtaining a second binding result; and (c) comparing the first and second binding results to determine whether Grb2 protein is present in the material.

The peptides of the present invention inhibit cell motility. The peptides prevent scattering of cells.

The cytotoxic effects of agents that disrupt the cytoskeleton, such as colchicine, taxol, cytochalasins, and phalloidin are well-characterized, and are fundamentally different from the anti-motility effects exerted by the peptides employed in the present invention. These peptides may be highly efficacious for the safe treatment of human diseases such as metastatic cancers, e.g., where the role of HGF plays a role in stimulating the invasion of cells into tissue surrounding the tumors and the migration of metastases to distant sites.

EXAMPLES

The following examples further illustrates the present invention but, of course, should not be construed as in any way limiting its scope.

Example 1

This Example illustrates the inhibition of cell motility in accordance with a method of the present invention.

Materials

HGF/NK1 was produced in a bacterial expression system, purified and refolded as described in Stahl et al., *Biochem. J.*, 326: 763–772 (1997). Peptides 1–4 were synthesized and purified as described in Yao et al., supra. The Grb2 binding properties of these compounds in vitro have been described previously (Yao et al. supra). Among these peptides, 4 has the lowest affinity for Grb2 by at least 100-fold. Accordingly, this peptide was used as a negative control in the biological experiments discussed herein.

MDCK Cell Scatter Assay

MDCK cell movement, observed as the dispersion or scatter of single cells from tightly grouped colonies, was assayed as described in Stoker et al., *J. Cell Sci.*, 77, 209–223 (1985). Briefly, MDCK cells were seeded at the final density of $2 \times 10^4$ cells/well into 24 well plates in OMEM containing various concentrations of inhibitors. Four hours later HGF (30 ng/ml) was added, and cells were incubated for and additional 16 h at 37° C. The scatter of fixed and stained cells was observed by light microscopy.

Cell Migration Assay

Migration by 185B5 and Okajima cells was measured using Biocoat Cell Environments control inserts (8 micron pore size; Becton Dickinson). The lower chamber contained RPMI+0.10% FBS, to which growth factors or inhibitors were added. Cells were trypsinized, washed in RPMI+0.1% FBS, added to the upper chamber at a final density of $2 \times 10^5$ cells/ml, and incubated for 16 h at 37° C. Cells were fixed and stained using Diff-Quik (Dade Diagnostics of P.R. Inc.), and number of cells that had traversed the membrane were counted using low-power brightfield microscopy. The difference in this number between untreated and treated cells is designated on the y-axis as "Fold Increase" in migration. 32D/c-Met cell migration was assayed using a modified Boyden chamber with 5 micron pore size Nucleopore filters (Corning) as described in Uren et al., *Biochem. Biophys. Res. Comm.*, 204, 628–634 (1994). Growth factors or inhibitors were added to the lower chamber, and 32D/c-Met cells washed in serum-free medium were applied to the upper chamber at a final density of $2 \times 10^6$ cells/ml, and incubated for 8 h at 37° C. Cells in the lower chamber were counted with an automated cell counter (Coulter, Inc.) and migration was quantitated.

Cultured Cell Lines and cDNA Transfections

The human mammary epithelial cell line 184B5 was maintained in Roswell Park Memorial Institute (RPMI) 1640 medium (Gibco)+10% fetal bovine serum (FBS) and 5 ng/ml epidermal growth factor (Becton Dickinson). The murine IL-3-dependent cell line 32D was cultured in RPMI 1640+10% FBS and 5% WEHI-3B conditioned medium as a source of IL-3. 32D/c-Met cells were generated by co-transfection of 32D cells with pMOG human c-Met cDNA and the neomycin-resistance encoding pCEV27 cDNA by electroporation as described in Pierce et al., *Science*, 239, 628–631 (1988). Cells were selected in G418 and c-Met expression in stable cell lines was detected by immunoblotting.

The effect of the peptides on the migration of 32D/c-Met cells is shown in FIGS. 2A and 2B. The results are representative of three or more experiments. HGF/NK1 stimulated the cell migration in this system almost 20-fold over untreated control cells. The peptides 1–3 each reduced HGF/NK1-stimulated cell migration in a dose-dependent manner. The IC50 values calculated from these tests were about 1 to about 10 nM.

Figure 3A:
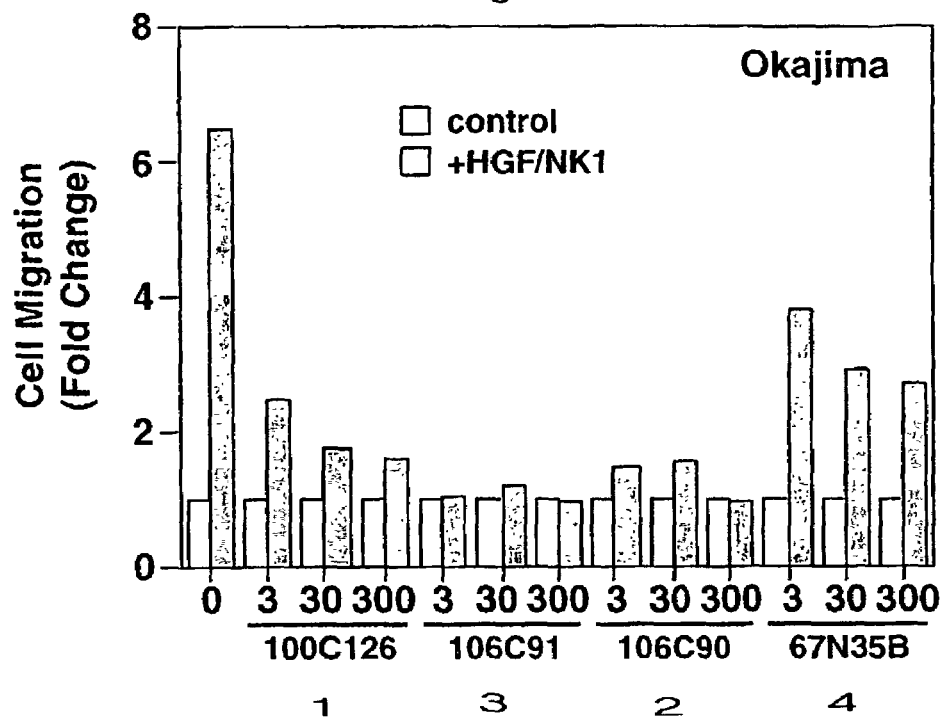
FIG. 3A depicts the effect of peptides 1–3 on the migration of Okajima cells and FIG. 3B depicts the effect of peptide 1 on the 184B5 cells.
Figure 3B:
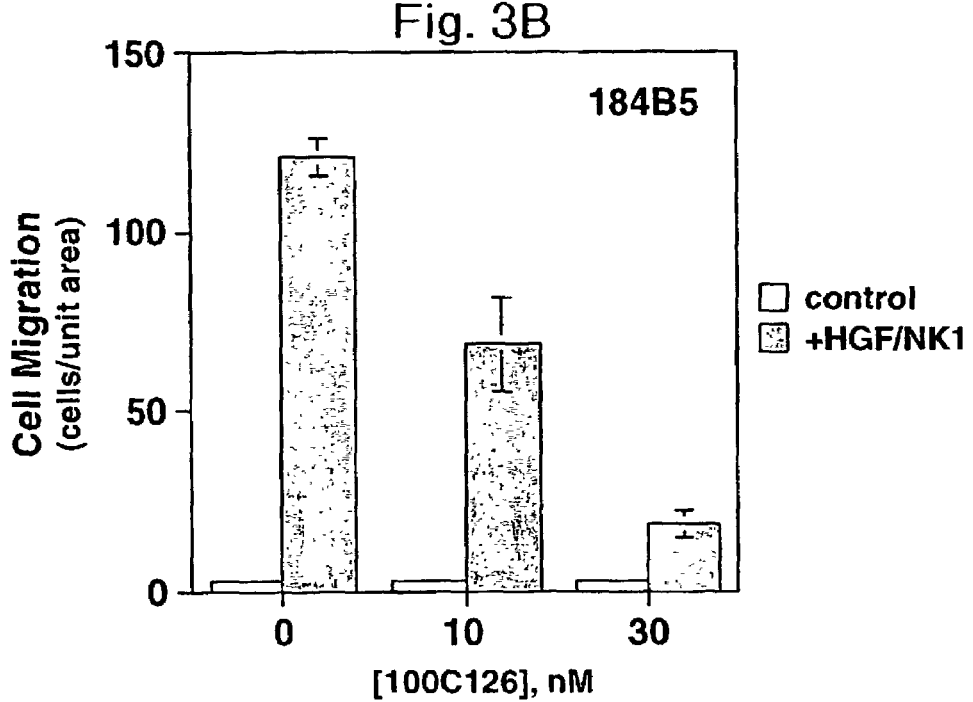

The effect of the peptides on the migration of human Okajima cells and 184B5 mammary epithelial cells is shown in FIGS. 3A and 3B. Results are representative of three or more experiments. In both panels, values represent the number of migrating cells per unit area on the bottom surface of the membrane barrier. Mean values from 10 randomly selected unit areas are calculated from each of three identically-treated wells. Okajima is a highly transformed cell line derived from a human gastric carcinoma in which the HGF receptor, c-Met, is dramatically overexpressed (approximately 100-fold) relative to normal epithelial HGF target cells, such as 184B5. As shown in FIG. 3A, the peptides each reduced HGF/NK1-stimulated Okajima cell migration in a dose-dependent manner. The IC50 values calculated from these experiments were in the range of 10 to 30 nM. The same compounds were equally effective in blocking HGF/NK1-stimulated migration by 184B5 cells (FIG. 3B).

Figure 4:
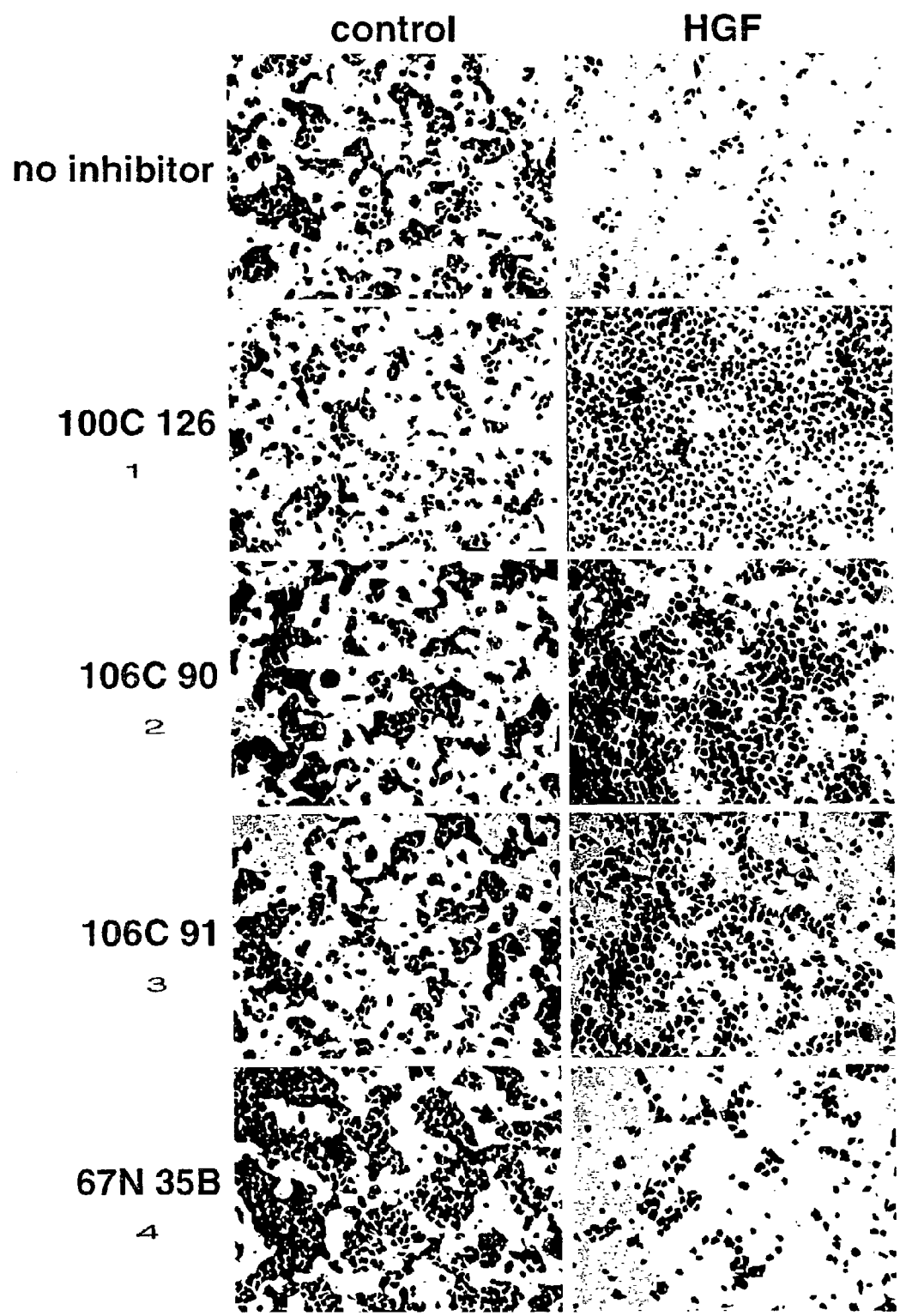
FIG. 4 depicts photomicrographs of the effect of peptides 1–3 on the scatter of MDCK cells. Panels on the left side show cells not treated with HGF, and panels on the right show cells treated with HGF at 30 nM (final concentration). The peptides were added at 10 nM (final concentration). Also included in FIG. 4 are the results obtained on peptide 4.

HGF exerts a unique and potent effect on the morphology, dispersion, and movement of Madin-Darby canine kidney (MDCK) epithelial cells known as "scatter" (Stoker et al., supra). In FIG. 4, MDCK cell movement, observed as the dispersion or scatter of single cells from tightly grouped colonies, was assayed. Photomicrographs show representative areas from one of triplicate samples for each condition. The results reported are representative of three experiments. As shown in FIG. 4, HGF-stimulated MDCK cell scatter was blocked by the peptides at 10 nM each. The peptides reduced the number of single cells, i.e. those with the highest level of motility. These data show that the peptides potently blocked HGF-stimulated migration by both epithelial and hematopoietic cell types, derived from both normal and tumor tissue.

The level of cell migration observed in the absence of HGF stimulation was not significantly affected by the active mimetics. These data suggest that these peptides act at the level of HGF regulation of cell motility, not at the level of the motility apparatus itself. The cells in all assays remained viable and fully capable of cell division following extended (up to 48 hours) treatment with these peptides, confirming that they lack cytotoxic effects.

While the active peptides did not appear to block the HGF-stimulated spreading of MDCK cells, one of the earliest events in the process of cell scatter (Ridley et al., *Mol. Cell. Biol.*, 15, 1110–1122 (1995)), they appeared to dramatically reduce the number of single cells, i.e. those with the highest level of motility. Together these data show that the mimetics 1–3 potently block HGF-stimulated migration by both epithelial and hematopoietic cell types, derived from both normal and tumor tissue.

Example 2

This Example illustrates the inhibition of matrix invasion and tubulogenesis by epithelial and endothelial cells, processes that are associated with angiogenesis.

Materials

The truncated HGF isoform HGF/NK1 was produced in a bacterial expression system, purified and refolded as previously described in Example 1. Peptides 1–4 were synthesized and purified as described in Example 1 and Yao et al, supra. Human recombinant basic fibroblast growth factor (bFGF) and human recombinant vascular endothelial growth factor (VEGF) were from R&D Systems (Minneapolis, Minn.).

Cultured Cells Lines

TAC-2 (Soriano et al., *J. Cell Science*, 108: 413–430 (1995)), a normal mammary gland epithelial cell line, was cultured in high-glucose DMEM (Gibco BRL Life Technologies, Gaithersburg, Md.) supplemented with 10% fetal bovine serum (FBS) (Biofluids, Rockville, Md.). Madin-Darby canine kidnev (MDCK) epithelial cells were maintained in DMEM+100% FBS. Human dermal microvascular (HMEC-1) endothelial cells (Adeset al., *J. Invest. Dermatol.*, 99: 683–690 (1992)) were grown in RPMI 1640 (Biofluids) containing 10%/o FBS and 2 mM glutamine. Human microvascular endothelial (HMVE) cells from neonatal dermis were purchased from Cascade Biologicals and cultured in Medium 131, containing with MVGS (media supplement) and 10% Glutamine, as indicated by the manufacturer. Human umbilical vein endothelial (HUVE) cells were isolated from freshly delivered cords as reported previously (Jaffee et al., *J. Clin. Invest.*, 52: 2745–2756 (1973)) and grown on Nunclon dishes (Nunc, Dem-nark) in RPMI 1640 supplemented with $^{20}$% bovine calf serum (Hyclone Laboratories, Logan, Utah), 50 µg/ml gentamycin, 2.5 µg/ml amphotericin B (fungizone) (Life Technologies), 5 U/ml sodium heparin (Fisher Scientific, Pittsburgh, Pa.), and 200 µg/ml endothelial cell growth supplement (ECGS) (Collaborative Research, Bedford, Mass.) and were used between passages 3 and 6.

Extracellular Matrix Invasion Assay

MDCK cell invasion into three-dimensional collagen gels was analyzed as previously described. Briefly, type I collagen (1.5 mg/ml; Cohesion Technologies) was mixed with 10× MEM and sodium bicarbonate (11.76 mg/ml) at a ratio of 8:1:1 (vol:vol:vol) on ice, and 0.4 ml aliquots were dispensed into 16-mm tissue culture wells (Nunc), and allowed to gel at 37° C. for 20 min. Cells were seeded onto gels ($1\times10^4$ cells/well) in 0.4 ml of growth medium containing HGF and/or peptides 1 or 4 as indicated. After 5 days, cells were fixed in situ in 2.50/o glutaraldehyde in 0.1 M sodium cacodylate buffer (pH 7.4), and cells that had invaded the gel below the surface monolayer in ten randomly selected fields (1×1.4 mm) were counted microscopically using a 20× phase contrast objective. Depth of cellular invasion into the collagen gel was quantitated in the same ten fields per treatment group using a calibrated fine focusing micrometer. Values were compared using the Student's unpaired t-test and a significant value was taken as $P<0.001$. Results in Table 1 are shown as the mean number of invading cells/field or mean invasion depth/cell in microns+ standard error of the mean.

TABLE 1

MDCK Cell Invasion into Collagen Matrices

| Treatment Group | Mean Invading Cells/Field | Mean Invasion Depth/Cell (µm) |
| --- | --- | --- |
| Control | 0 | 0 |
| HGF | 29.7 ± 2.6 | 35.6 ± 2.7 |
| HGF + peptide 2 | 12.6 ± 1.9 | 17.9 ± 1.9 |
| HGF + peptide 4 | 34.3 ± 2.7 | 30.8 ± 2.9 |

MDCK cells were left untreated (Control), treated with HGF (10 ng/ml), or HGF + peptide 2 or 4 (100 nM), and invasion into collagen matrices was quantitated microscopically as described above. Values are the mean of at least 10 randomly selected fields ± standard error of the mean.

Epithelial Tube Formation Assay

Figure 5:
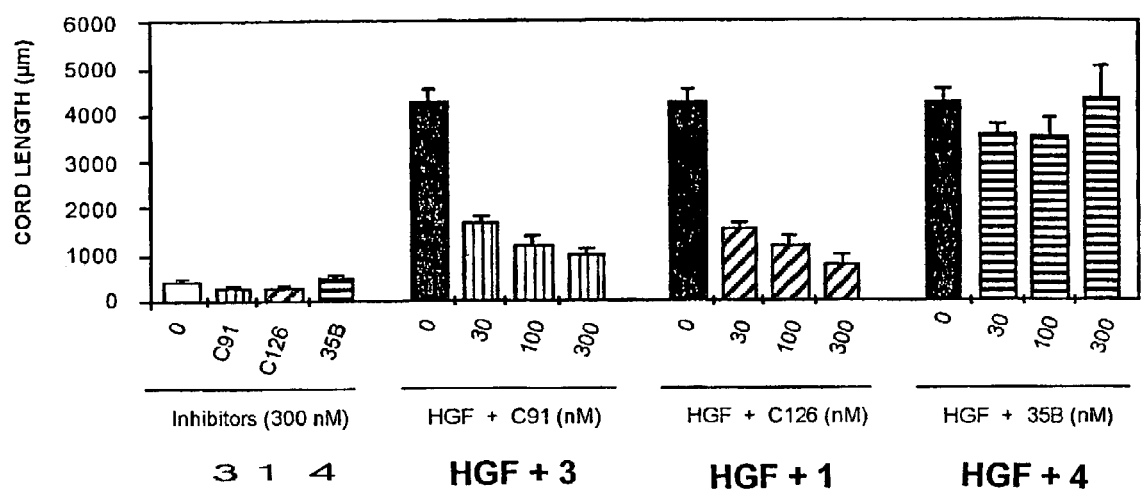
FIG. 5 depicts the effect of peptides 1, 3, and 4 on the cord length (in μm) formed by TAC-2 cells pre-treated for 18–24 hours with or without the indicated concentrations of peptides 1, 3, or 4. Peptide concentrations are indicated on the X-axis in nM. Y-axis values are mean cord length per field s.e.m.

TAC-2 cells were suspended in three-dimensional collagen gels at $1\times10^4$ cells/ml in collagen and incubated in complete medium containing HGF and/or Grb2 inhibitors as indicated. After 3 days, the cultures were fixed with 2.5% glutaraldehyde in 0.1 M cacodylate buffer, and at least 3 randomly selected fields per experimental condition in each of 3 separate experiments were digitally recorded with brightfield microscopy. The total length of the cords in each individual colony present in each optical field was measured with IPLab. Cord length was considered as "0" in: a) colonies with a spheroidal shape, and b) slightly elongated structures in which the length to diameter ratio was less than 2. The mean values for each experimental condition were compared to controls using the Student's unpaired t-test. Results in FIG. 5 are described as mean total cord length (in µm) per field.

Cell Migration Assays

The migration assay of HUVE and HMEC-1 cells in modified Boyden chambers was adapted from previously described procedures (Murohara et al., *Thromb. Vasc. Biol.*, 19: 1156–61 (1999), Malinda et al., *FASEB J.*, 13: 53–62 (1999)). In brief, Biocoat Cell Environment control inserts (8 micron pore size; Becton Dickinson) were coated with 0.1% gelatin (Sigma) for at least 1 hour at 37° C. and air dried. Lower chambers contained 0.7 ml RPMI+0.1% BSA, to which 20 ng/ml HGF and/or 300 nM Grb2 inhibitors were added. Cells were pre-treated with the indicated concentrations of Grb2 inhibitors for 18–24 hours, trypsinized, washed twice in RPMI+0.1% BSA, added to upper chambers ($5\times10^4$ cells/well) with or without inhibitors in a final volume of 0.5 ml, and incubated for 4 h at 37° C. Cells on the upper surface of each filter were removed with a cotton swab, while cells that had traversed to the bottom surface of the filter were fixed and stained using Diff-Quik (Dade Diagnostics) and counted using a 10× objective. Mean values from 4 randomly selected fields (1×1.4 mm) were calculated for each of triplicate wells per experimental condition. Shown in FIG. 6 is the ratio of growth factor-treated to control migrating cells designated on the y-axis as "Migration (Fold Increase)" or as the mean number of cells per optical field in FIGS. 8–11.

Figure 12A:
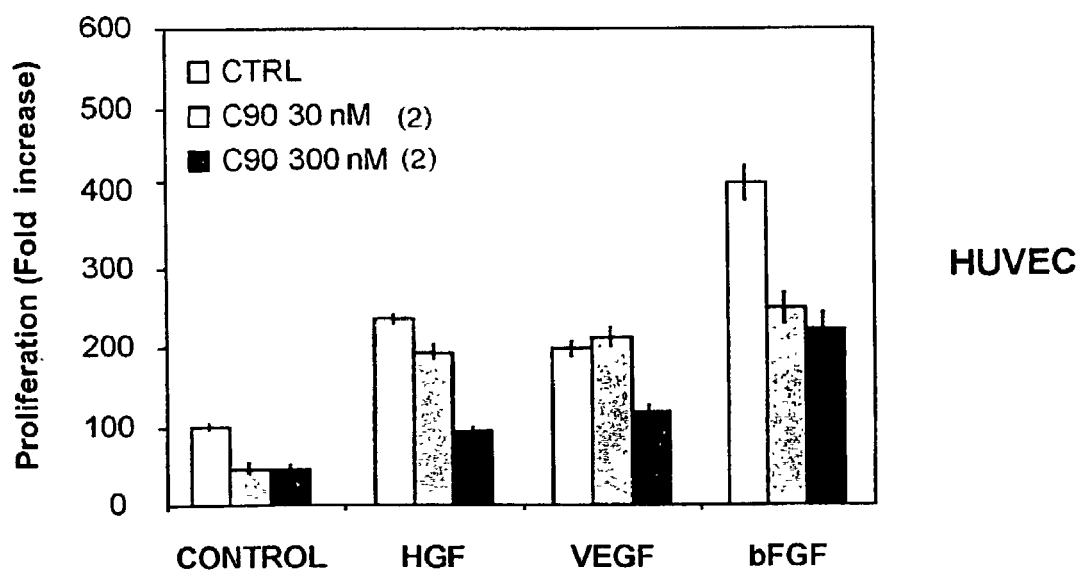
FIG. 12 depicts the effect of peptide 2 on HGF-, bFGF- and VEGF-induced HUVE and HMVE cell proliferation.
Figure 12B:
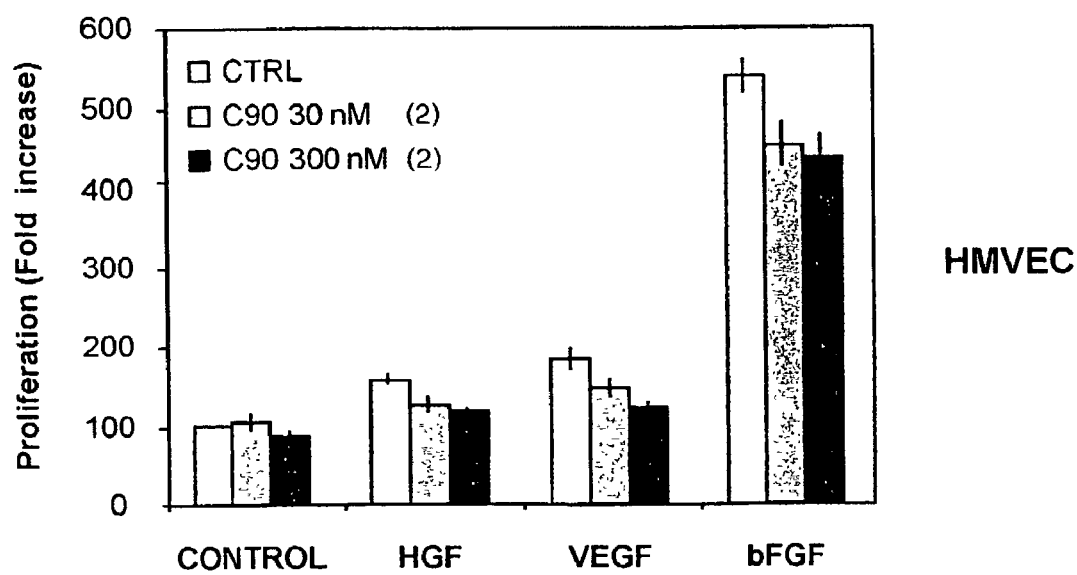

HUVE or HMVE cells were seeded per triplicate in type I collagen-coated 48-well plates (Biocoat) (3000 cells/well) in 500 µl of complete EGM-Bullet Kit medium (BioWhittaker, Walkersville, Md.), allowed to attach for 4 hr and incubated overnight with or without the indicated concentrations of peptide 2. The cultures were rinsed twice in serum-free medium and incubated with EBM medium (Bio-Whittaker) supplemented with 50 µg/ml heparin, 50 µg/ml ascorbic acid and 10% FCS. After either 4 days (HUVE) or 5 days (HMVE), cells were harvested with trypsin/EDTA and counted with an hemocytometer. The mean number of cells per ml was calculated from 3 independent measures for each of triplicate wells per experimental condition and compared to controls using the Student's unpaired t-test. Results set forth in FIG. 12 are described as the ratio of growth factor-treated to control proliferating cells designated on the y-axis as "Proliferation (Fold Increase)".

Endothelial Cell Tubulogenesis Assay on Collagen

Figure 7:
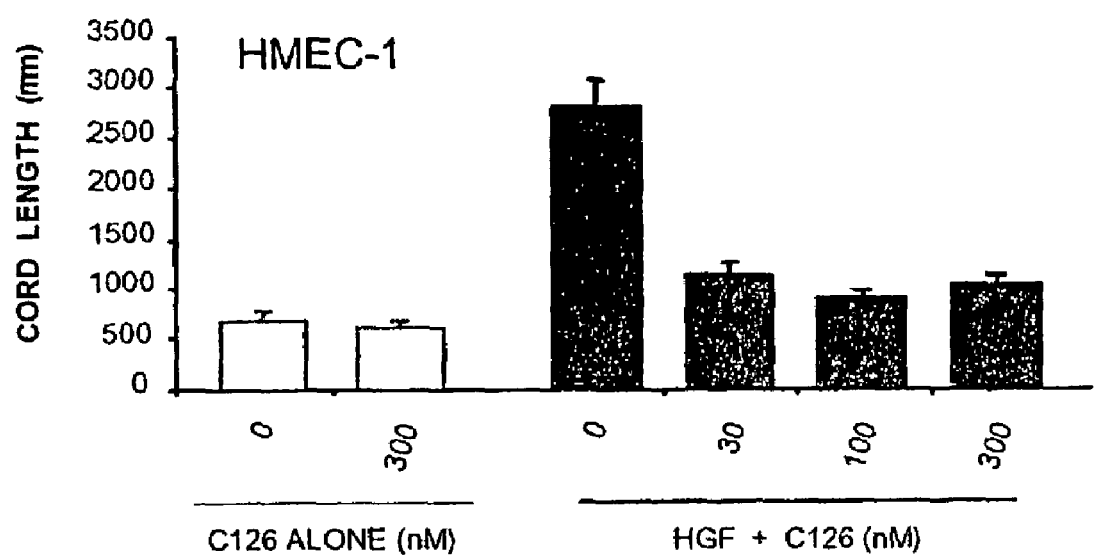
FIG. 7 depicts the effect of peptide 1 on collagen matrix invasion by HMEC-1 cells. Unfilled bars represent matrix invasion by HMEC-1 cells in the absence of HGF. Shaded bars represent matrix invasion by HMEC-1 cells in the presence of HGF. The X-axis represents peptide concentration in nM. The Y-axis represents the mean length of all the cords or single cells invading the collagen at 20 μm beneath the surface of the gel.

HMEC-1 cell tubulogenesis assay on collagen gels was adapted from a previously described procedure (Montesano et al., *Cell*, 42: 469–77 (1985), Pepper et al., *Exp. Cell Res.*, 204: 356–63 (1993)). Cells were seeded onto collagen gels cast in 16-mm wells ($2.5\times10^4$ cells/well) and grown to confluence in reduced growth medium (5% FCS and 150 µg/ml ECGS). At confluence cells were pre-treated with or without Grb2 inhibitors for 24 hours, after which time medium was replaced by fresh medium supplemented with or without the indicated concentration of inhibitors and/or 20 ng/ml HGF. Medium and compounds were changed every day. After 24 hours, the cultures were fixed in situ, and 5 randomly selected optical fields per experimental condition in each of three separate experiments were digitally recorded under phase contrast microscopy using a 20× phase contrast objective, by focusing 20 µm beneath the surface of the gel. Invasion was quantitated using IPLab software (Scanalytics, Fairfax, Va.) by measuring the total length of all cellular structures that had penetrated beneath the surface monolayer either as apparently single cells or in the form of cell cords. Values were compared using Student's unpaired t-test and a significant value was taken at P<0.001. Results set forth in FIG. 7 are the mean total length (in µm) per field.

HUVE Cell Tubulogenesis Assay on Matrigel

The HUVE tube formation assay was performed as previously described (Grant et al., *J. Cell. Physiol.*, 153: 614–625 (1992)). Briefly, 96-well plates were coated with 90 µl of Matrigel (10 mg/ml) (Collaborative Research) (Baatout, supra) and incubated at 37° C. for 30 min to promote gelling. 10,000 HUVECs were resuspended in reduced growth medium (serum concentration 10% and 5 U/ml heparin) and added to each well with the indicated reagents in a final volume of 100 µl. After 18 h, the plates were fixed with Diff-Quik, and at least 4 randomly selected fields per experimental conditions were digitally recorded under bright field illumination using a 10× objective. The mean additive length of the cords present in each optical field was measured using IPLab and compared to controls using the Student's unpaired t-test.

The ability of MDCK cells to invade three-dimensional collagen matrices, a prerequisite for HGF-stimulated branching morphogenesis, was assessed in the presence of peptides 3 and 4 (Table 1). After 5 days in culture in the absence of HGF, MDCK cells remain as a monolayer on the surface of the collagen gel, but HGF stimulates a high proportion of these cells to invade the gel (35 mm mean depth of invasion; Table 1). Peptide 3 (100 nM) reduced both the number of invading cells, as well as the mean depth of invasion per cell, by at least 50%, while peptide 4 had no significant effects (Table 1). MDCK cell viability throughout the 5-day culture period was unchanged in the absence or presence of the Grb2 SH2 domain antagonists. Together with the results of Example 1, these data demonstrate that Grb2 SH2 domain antagonists inhibit two main biological effects of HGF, namely the induction of cell migration and the invasion of extracellular matrix.

The ability of Grb2 SH2 domain antagonists to abrogate the morphogenetic activities of HGF was assessed. In a first set of experiments, we used an in vitro model of ductal morphogenesis in which mammary gland-derived epithelial (TAC-2) cells grown within a three-dimensional collagen gel are induced to form branching duct-like structures by HGF. When grown in collagen gels under control conditions, TAC-2 cells formed small, irregular cell aggregates. In the presence of 20 ng/ml recombinant human HGF they gave rise, after 3 days, to long branching tubes. In marked contrast, co-addition of peptide 1 and HGF to the cultures abrogated the elongation and branching of duct-like structures. A quantitative analysis of tube formation demonstrated that peptides 1, 2, and 3 significantly (p<0.0001) abrogate HGF-induced elongation of epithelial tubes in a dose-dependent manner, a sub-maximal inhibitory effect being already observed with 30 nM of inhibitor, and a maximal effect with 3 mM, whereas low affinity binding peptide 4 had detectable effect at these concentrations (FIG. 5, and data not shown).

Figures 6A, 6B:
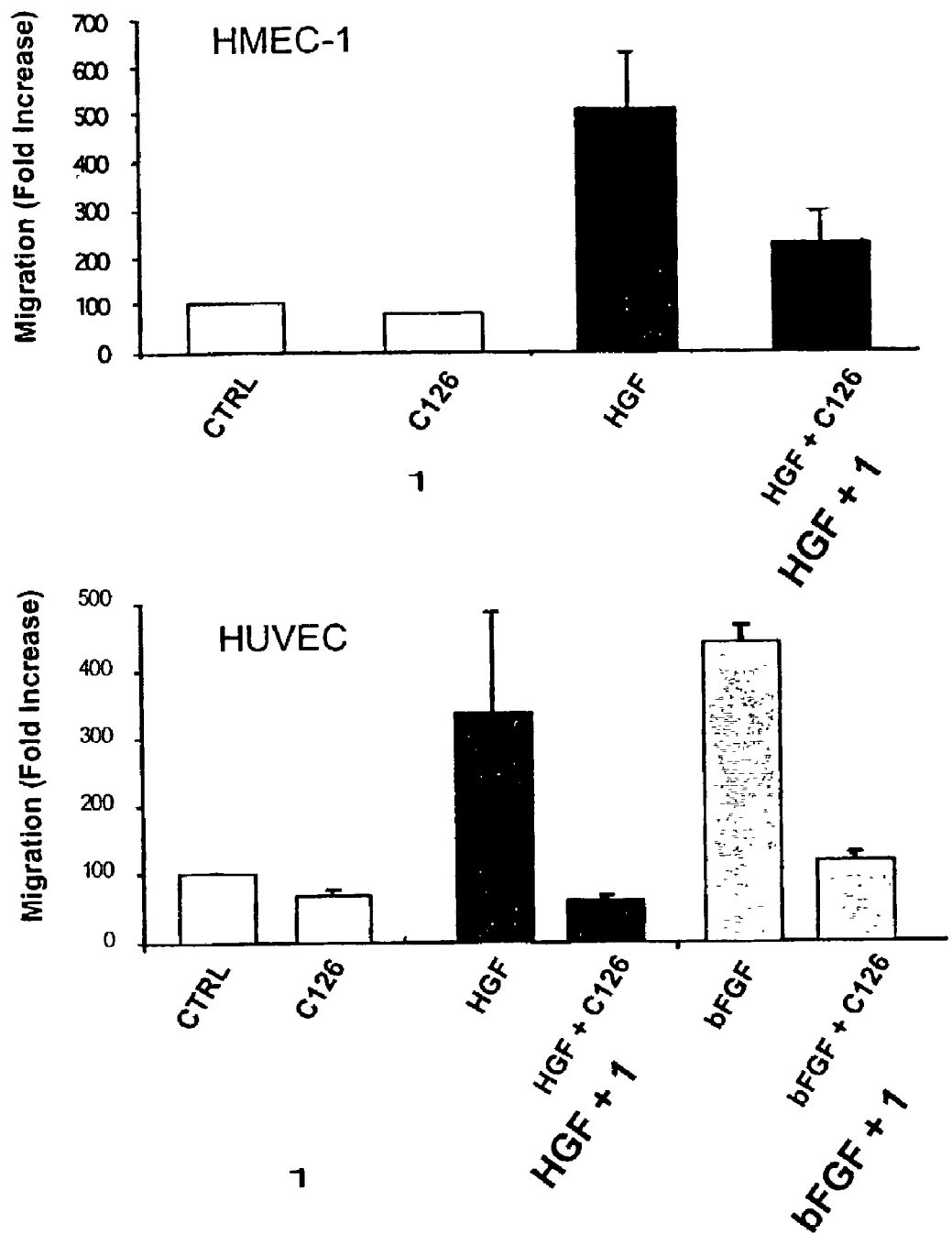
FIG. 6A depicts the effect of peptide 1 on HGF-induced HMEC-1 cell migration.
FIG. 6B depicts the effect of peptide 1 on HGF— and bFGF-induced HUVEC migration. In both FIGS. 6A and 6B, the X-axis represents treatment conditions. The Y-axis represents the fold increase of HMEC-1 migration expressed as the ratio of migrating cells in HGF-treated wells (FIG. 6A) or bFGF-treated wells (FIG. 6B) to control treated wells.

The effect of peptide 1 on the chemokinetic response of immortalized human microvascular (HMEC-1) and primary human umbilical vein endothelial cells to angiogenic factors was assessed. It was observed that this compound (300 nM) did not significantly alter the basal levels of endothelial cell motility (FIGS. 6A–B, open bars). However, it practically reverted to basal levels the 5.5- and 3.5-fold increase on cell motility induced by 20 ng/ml HGF on HMEC-1 and HUVECS, respectively. Interestingly, this inhibitory activity does not seem limited to HGF stimulation, as demonstrated by the complete blockade of bFGF-induced HUVEC migration by 300 nM of peptide 1 (FIGS. 6A–B, closed bars). These results suggest that Grb2 inhibitors may prevent endothelial cell motility in response to angiogenic stimuli conveyed by different receptor tyrosine kinases.

To assess whether the blockade of endothelial cell motility by Grb2 inhibitors might correlate with a loss of morphogenetic response to an angiogenic factor, two alternative models of in vitro endothelial angiogenesis were used. In the first model, microvascular endothelial cells were seeded onto the surface of a collagen type I gel. The cultures were treated only after they had reached confluence (approx. 1 week later). After a further 5-day incubation, HMEC-1 cells grown under control conditions had discretely invaded the subjacent collagen matrix as single cells. Addition of 20 ng/ml HGF to the cultures induced a 6-fold increase in collagen invasion by either single cells or short cell cords devoid of lumen. Co-addition of peptide 1 (30–300 nM) and HGF to the cultures suppressed collagen invasion induced by HGF, a significant (p<0.001) decrease in the total length of the cords present 20 µm below the surface of the gel already being observed at a concentration of 30 µM (FIG. 7). Thus, although HGF failed to induce the formation of lumen-containing capillary-like structures by HMEC-1 cells, its stimulatory effect on matrix invasion, a process required during angiogenesis, was blocked in the presence of peptide 1, a Grb2 antagonist.

In the second in vitro model of angiogenesis, HUVECs were seeded onto a Matrigel gel layer, and immediately treated with HGF, HGF/NK1, or HGF/NK1 with peptide 1. Under control conditions, the cells migrated on the surface of the gel, established contact with each other and, after 12–18 hours, formed irregular ridges or cords, a process reminiscent of the early steps of angiogenesis. Addition of 20–50 ng/ml HGF (not shown) or 300 ng/ml HGF/NK1 to the cultures resulted in the formation of a continuous, extensive network of thick cords. In contrast, co-addition of HGF/NK1 and peptide 1 (1 µM) markedly reduced the extent of cord formation. A quantitative analysis of mean length of the cords per optical field demonstrated a significant (p<0.001) 300% increase induced by HGF/NK1 (3217.0±166.5 µm in HGF/NK1-treated cultures vs. 1189.5±166 µm in controls), and a significant (p=0.001) 30% decrease when co-addition of peptide 1 and HGF/NK1 was compared to HGF/NK1 alone (3217.0±166.5 µm in HGF/NK1 alone vs. 2502.8±108 µm in HGF/NK1 plus peptide 1). Similar results, although to a lower extent, were observed when HGF or HGF/NK1 were substituted by 50 ng/ml bFGF (data not shown).

Taken together, these results demonstrate that a peptide having cell signal inhibiting activity and cell motility inhibiting activity, namely Grb2 SH2 domain antagonists, inhibit the formation of epithelial branching duct-like structures and alter endothelial capillary-like cords induced by the HGF isoform HGF/NK1.

Figure 8A:
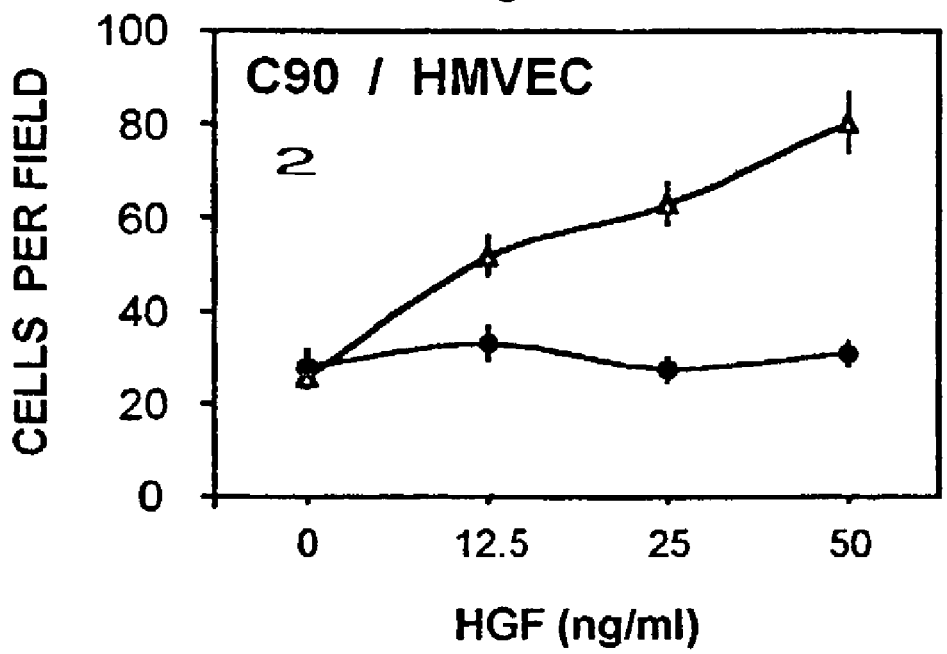
FIG. 8A depicts the effect of peptide 2 on HGF-induced HMVEC migration.
Figure 8B:
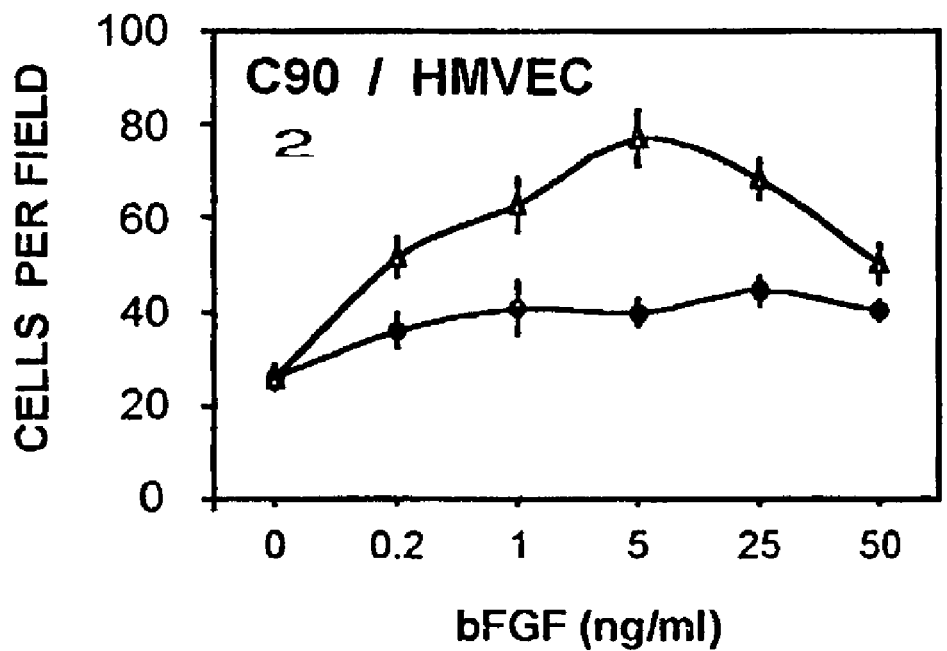
FIG. 8B depicts the effect of peptide 2 on bFGF-induced HMVEC migration.

To further characterize the anti-angiogenic effect of the Grb2 antagonists, the effect on human neonatal microvascular (HMVE) cell migration was assessed in the presence or the absence of increasing concentrations of either HGF (0–50 ng/ml) or bFGF (0.2–50 ng/ml) and peptide 2 (300 nM). It was observed that peptide 2 abolished (p<0.001) cell migration induced by HGF (FIG. 8A) and significantly (p<0.001) inhibited the biphasic stimulatory activity of bFGF. Remarkably, the effect of the optimal concentration of bFGF (5 ng/ml) was abolished by 72%. (FIG. 8B). The effect of peptide 2 on the activity of the most powerful angiogenic molecule known to date, namely, vascular endothelial growth factor (VEGF) was assessed. When incubated in modified Boyden chambers in the presence of VEGF, HMEC-1, HMVE and HUVE cells underwent different, albeit significant, degrees of migration (FIG. 9). However, the addition of peptide 2 significantly (p<0.001) reverted the effect of VEGF in all the cell lines, although the degree of inhibition of VEGF activity differed among the endothelial cell lines. Similar results were observed with antagonist 1 (FIG. 9 and data not shown). These results show that Grb2 inhibitors prevent endothelial cell motility in response to angiogenic stimuli conveyed by different angiogenic pathways, and that this antagonistic activity is not restricted to a single type of endothelial cell.

Figure 10:
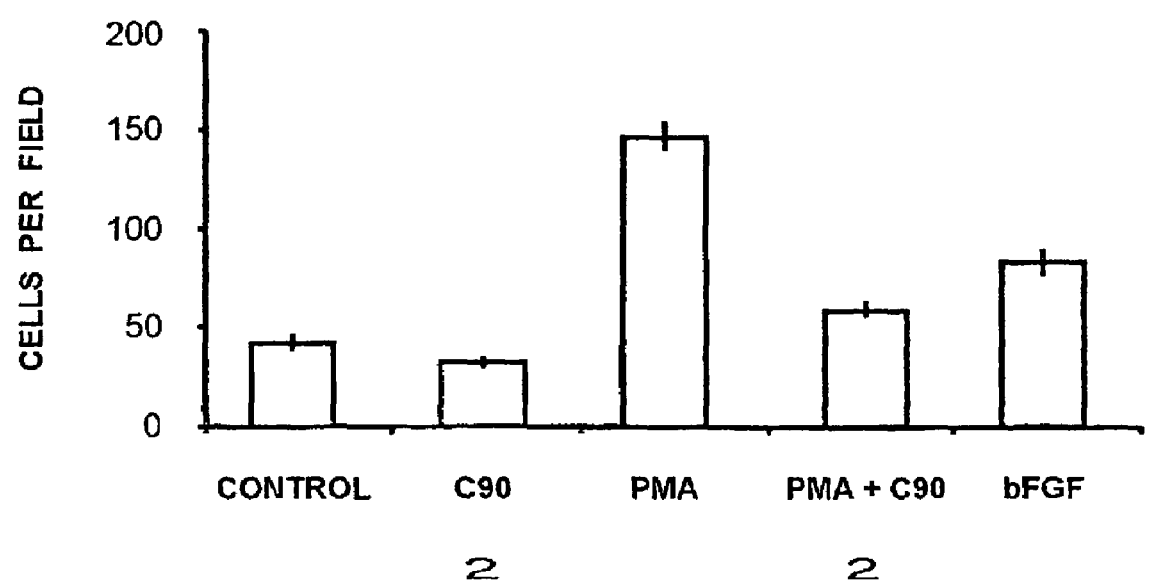
FIG. 10 depicts the effect of peptide 2 on PMA-induced HUVE cell migration

To determine whether the effect of Grb2 antagonists is restricted to the inhibition of endogenous angiogenic factors or might also revert the effect of exogenous pro-angiogenic molecules, the effect of peptide 2 on the migratory properties of HUVE cells was assessed in the presence of phorbol myristate acetate (PMA), a potent tumor promoter. In vitro, upon exposure to PMA, both microvascular and macrovascular endothelial cells undertake a vascular morphogenetic program by invading the surrounding extracellular matrix and subsequently forming extensive network of capillary-like tubular structures (Montesano et al., Cell, 42:469–77 (1985) and references mentioned therein). Addition of PMA (40 ng/ml) to cultures of HUVE cells in modified Boyden chambers, resulted in a 300% increase of cell migration. This pro-angiogenic activity, which cannot be mimicked by the maximal concentration (5 ng/ml) of bFGF, was dramatically reverted to basal levels in the presence of 300 nM peptide 2 (FIG. 10).

The effect of Grb2 antagonists on the inhibition of other biological properties of endothelial cells relevant to the process of angiogenesis was assessed. To understand the activity of peptide 2 during growth factor-induced endothelial cell proliferation, HUVE and HMVE cells were cultivated on type I collagen-coated wells in partially supplemented endothelial culture (EBM) medium, as described in Material and Methods. Under these stringent culture conditions, HGF (25 ng/ml), VEGF (10 ng/ml) and bFGF (5 ng/ml) induced a significant (p<0.0001) increase in endothelial proliferation, as evidenced by a 2.3-, 2- and 4.1-fold increase, respectively in the mean number of macrovascular HUVE cells per ml. Similar, significant (p<0.001) increases in cell numbers were observed in HMVE cells (FIG. 12, open bars). Addition of Grb2 inhibitor peptide 2 (30 nM, 300 nM) resulted in a significant, albeit markedly different, inhibition of proliferation in HUVE and HMVE cells. Whereas peptide 2 inhibited serum-dependent (p<0.001) and bFGF-dependent (p<0.0001) HUVE cell proliferation at concentrations of 30 nM, it failed to significantly (p=0.05) inhibit HGF- VEGF-induced proliferation at this concentration (FIG. 12, gray bars). Only higher concentrations of compound (300 nM) were able to induce significant (p<0.0001) reduction in cell counts (FIG. 12, black bars). However, the behavior of microvascular HMVE was dramatically different. While basically resistant (P=0.02–0.05) to 30 nM of the inhibitor both in the presence and absence of growth factors, highly significant (p<0.001) inhibition of cell growth was only observed with 300 nM of compound (FIG. 12, black bars). These results demonstrate that Grb2 inhibitors elicit different antagonistic effects on angiogenesis pathways depending both on the type of endothelial cell and the growth factor.

Figure 11:
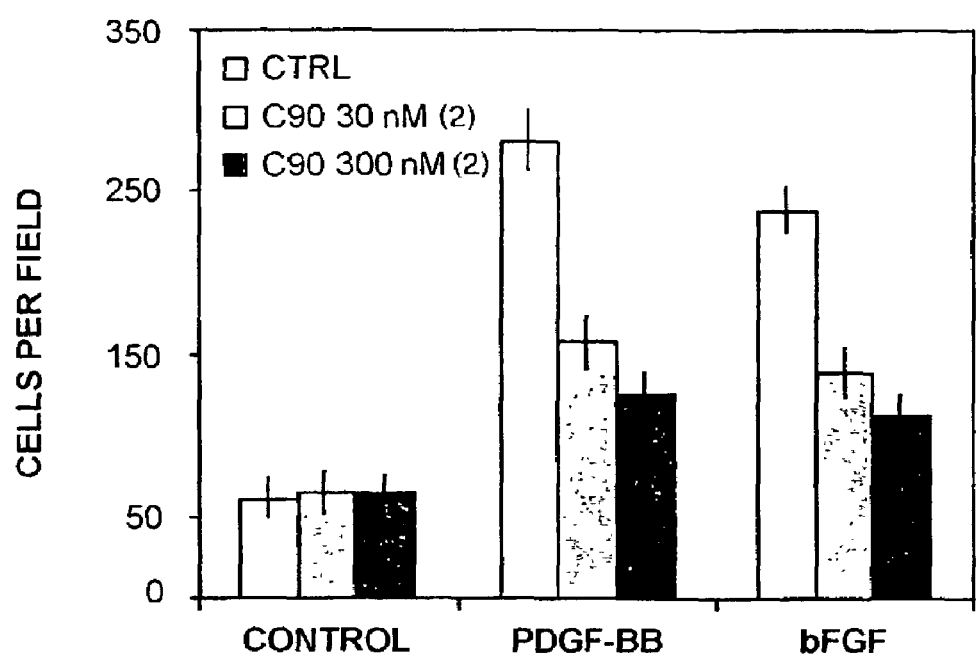
FIG. 11 depicts the effect of peptide 2 on PDGF-BB- and bFGF-induced cell migration in NIH 3T3 fibroblasts.

PDGF is implicated in different biological processes such vascular remodeling, wound healing and cancer (for reviews, see Bornfeldt et al., Ann N Y Acad. Sci., 766: 416–30, 1995; Gendron, Surv. Ophthalmol., 44:184–5, 1999). Addition of 50 ng/ml PDGF-BB to NIH 3T3 fibroblasts incubated in a modified Boyden chamber results in a dramatic, 20-fold increase in cell migration. When co-added simultaneously to the cultures, the Grb2 antagonist peptide 2 inhibits NIH 3T3 cell migration in a significant (p<0.001), dose-dependent manner, a 60% reduction in the mean number of cells per field being already observed with concentrations as low as 30 nM and a further (FIG. 11). This observation opens a potential therapeutical use of the Grb2 inhibitor compounds in the treatment of diseases such as cancer, wound healing disorders, vascular complications of diabetes mellitus, vascular nephropathies, and diseases with occurrence of fibrosis.

The references cited herein, including patents, patent applications, and publications, are hereby incorporated by reference in their entireties. While this invention has been described with an emphasis upon several embodiments, it will be obvious to those of ordinary skill in the art that variations of the embodiments may be used and that it is intended that the invention may be practiced otherwise than as specifically described herein. Accordingly, this invention includes all modifications encompassed within the spirit and scope of the invention as defined by the following claims.

What is claimed is:

1. A method of inhibiting cell motility in a mammal comprising administering to said mammal a peptide of formula (I) having cell signal inhibiting activity and cell motility inhibiting activity, wherein said peptide is substantially free of cytotoxicity;

(I)

wherein n is 1–6;
PTI is a phenylalanyl radical having a phenyl ring, an amine end, and a carboxyl end, the phenyl ring having one or more substituents selected from the group consisting of hydroxyl, carboxyl, formyl, carboxyalkyl, carboxyalkyloxy, dicarboxyalkyl, dicarboxyalkyloxy, dicarboxyhaloalkyl, dicarboxyhaloalkyloxy, phosphonoalkyl, and phosphonohaloalkyl, wherein the alkyl portion of the substituents may be unsubstituted or substituted with a substituent selected from the group consisting of halo, hydroxy, carboxyl, amino, aminoalkyl, alkyl, alkoxy, and keto;
X is a moiety attached to the nitrogen of PTI and is selected from the group consisting of alkylcarbonyl, oxalyl, alkylaminooxalyl, arylaminooxalyl, arylalkylaminooxalyl, alkoxyoxalyl, carboxyalkyl carbonyl, heterocyclyl carbonyl, heterocyclylalkyl carbonyl, arylalkyl heterocyclylalkyl carbonyl, aryloxycarbonyl, and arylalkoxycarbonyl, wherein the aryl and alkyl portions of the substituents may be unsubstituted or substituted with a substituent selected from the group consisting of halo, hydroxy, carboxyl, amino, aminoalkyl, alkyl, alkoxy, and keto; and the heterocyclyl portion of X contains at least 4 hetero atoms selected from the group consisting of O, N, and S;
AA is an amino acid, the amine end of which is attached to the carboxyl end of PTI; and
Y is an arylalkylamino or arylheterocyclyl alkylamino, which may be unsubstituted or substituted;
or a salt thereof, with provisos that when X is acetyl, n=2, the AA attached to the carboxyl end of PTI is aminocyclohexane carboxylic acid, and Y is hydroxynaphthylpropylamino, the substituent on the phenyl ring of PTI is not phosphonomethyl and when X is oxalyl, n=2, the AA attached to the carboxyl end of PTI is aminocyclohexane carboxylic acid, and Y is naphthylpropylamino, the substituent on the phenyl ring of PTI is not dicarboxymethoxy.

2. A method of inhibiting angiogenesis in a mammal comprising administering to said mammal a peptide of formula (I) having cell signal inhibiting activity and cell motility inhibiting activity, wherein said peptide is substantially free of cytotoxicity;

(I)

wherein n is 1–6;
PTI is a phenylalanyl radical having a phenyl ring, an amine end, and a carboxyl end, the phenyl ring having one or more substituents selected from the group consisting of hydroxyl, carboxyl, formyl, carboxyalkyl, carboxyalkyloxy, dicarboxyalkyl, dicarboxyalkyloxy, dicarboxyhaloalkyl, dicarboxyhaloalkyloxy, phosphonoalkyl, and phosphonohaloalkyl, wherein the alkyl portion of the substituents may be unsubstituted or substituted with a substituent selected from the group consisting of halo, hydroxy, carboxyl, amino, aminoalkyl, alkyl, alkoxy, and keto;
X is a moiety attached to the nitrogen of PTI and is selected from the group consisting of alkylcarbonyl, oxalyl, alkylaminooxalyl, arylaminooxalyl, arylalkylaminooxalyl, alkoxyoxalyl, carboxyalkyl carbonyl, heterocyclyl carbonyl, heterocyclylalkyl carbonyl, arylalkyl heterocyclylalkyl carbonyl, aryloxycarbonyl, and arylalkoxycarbonyl, wherein the aryl and alkyl portions of the substituents may be unsubstituted or substituted with a substituent selected from the group consisting of halo, hydroxy, carboxyl, amino, aminoalkyl, alky, alkoxy, and keto; and the heterocyclyl portion of X contains at least 4 hetero atoms selected from the group consisting of O, N, and S;
AA is an amino acid, the amine end of which is attached to the carboxyl end of PTI; and
Y is an arylalkylamino or arylheterocyclyl alkylamino, which may be unsubstituted or substituted;
or a salt thereof, with provisos that when X is acetyl, n=2, the AA attached to the carboxyl end of PTI is aminocyclohexane carboxylic acid, and Y is hydroxynaphthylpropylamino, the substituent on the phenyl ring of PTI is not phosphonomethyl and when X is oxalyl, n=2, the AA attached to the carboxyl end of PTI is aminocyclohexane carboxylic acid, and Y is naphthylpropylamino, the substituent on the phenyl ring of PTI is not dicarboxymethoxy.

3. The method of claim 1, wherein said cell motility is one that is induced by the hepatocyte growth factor (HGF).

4. The method of claim 1, wherein cell motility is one that is induced by the binding of c-Met receptor with the Grb2 protein.

5. The method of claim 1, wherein X is oxalyl.

6. A method of inhibiting cell motility in a mammal comprising administering to said mammal a peptide of formula (I) having cell signal inhibiting activity and cell motility inhibiting activity, wherein said peptide is substantially free of cytotoxicity;

(I)

X is a moiety attached to the nitrogen of PTI and is selected from the group consisting of alkylcarbonyl, alkylaminooxalyl, arylaminooxalyl, arylalkylaminooxatyl, alkoxyoxalyl, carboxyalkyl carbonyl, heterocyclyl carbonyl, heterocyclylalkyl carbonyl, arylalkyl heterocyclylalkyl carbonyl, aryloxycarbonyl, and arylalkoxycarbonyl, wherein the aryl and alkyl portions of the substituents may be unsubstituted or substituted with a substituent selected from the group consisting of halo, hydroxy, carboxyl, amino, aminoalkyl, alkyl, alkoxy, and keto; and the heterocyclyl portion of X contains at least 4 heteroatoms selected from the group consisting of O, N, and S;

PTI is a bivalent radical of tyrosine or a bivalent radical of phosphotyrosine or of a phosphotyrosine mimetic in the form of a bivalent radical of an amino acid selected from the group consisting of phosphonomethyl-phenylalanine, phosphono-($\alpha$-fluoro)methyl-phenylalanine, phosphono-($\alpha,\alpha$-difluoro)methylphenylalanine, phosphono-$\alpha$-hydroxy)methyl-phenylalanine, O-sulfotyrosine, dicarboxymethoxy-phenylalanine, aspartic acid, glutamic acid, phosphoserine and phosphothreonine, each of which is present in the (D,L)-, D- or L-form;

-$(AA)_n$- is a bivalent radical of a tripeptide of the formula -$(AA^1)$-$(AA^2)$-$(AA^3)$-, wherein -$(AA^1)$- is selected from the group consisting of -Ile-, -$Ac_5c$-, -$Ac_6c$-, -Asp-, -Gly-, -Phe-, -$Ac_7c$-, -Nbo-, -Met-, -Pro-, -$\beta$-Ala-, -Gln-, -Glu-, -DHph-, -HPh- and -tLe-; -$(AA^2)$- is selected from the group consisting of -Asn-, -$\beta$-Ala-, -Gly-, -Ile-, and -Gln-; and -$(AA^3)$- is selected from the group consisting of -Val-, -$\beta$-Ala-, -Gly-, -Gln-, -Asp- and $Ac_5c$-; a bivalent radical of a dipeptide of the formula -$(AA^1)$-$(AA^2)$ wherein -$(AA^1)$ and -$(AA^2)$- are as recited above; or a bivalent radical of an amino acid selected from the amino acids mentioned above; and Y is a monosubstituted amino selected from the group consisting of lower alkylamino, octylamino, halonaphthyloxy-lower alkylamino, naphthyloxy-lower alkylamino, phenyl-lower alkylamino, di-phenyl-lower alkylamino, (mono- or di-halo-phenyl)-lower alkylamino, naphthalenyl-lower alkylamino, phenanthrenyl-lower alkylamino; cycloalkylamino; and cycloalkyl-lower alkylamino;

or a salt thereof.

7. The method of claim 1, wherein X is a moiety attached to the nitrogen of PTI and is selected from the group consisting of $C_1$–$C_6$ alkylcarbonyl, oxalyl, $C_1$–$C_6$, alkylaminooxalyl, arylaminooxalyl, aryl $C_1$–$C_6$, alkylaminooxalyl, $C_1$–$C_6$ alkoxyoxalyl, carboxy $C_1$–$C_6$ alkyl carbonyl, heterocyclyl carbonyl, heterocyclyl $C_1$–$C_6$ alkyl carbonyl, aryl $C_1$–$C_6$, alkyl heterocyclyl $C_1$–$C_6$ alkyl carbonyl, aryloxycarbonyl, and aryl $C_1$–$C_6$ alkoxycarbonyl.

8. The method of claim 1, wherein said peptide is selected from the group consisting of oxalyl-Pmp-Ile-Asn-NH-(3-naphthalen-1-yl-propyl), oxalyl-Pmp-Ile-Asn-NH-(3-(2-hydroxy-naphthalen-1-yl)-propyl), oxalyl-Pmp-Ile-Asn-NH-(3-naphthalen-2-yl-propyl), and oxalyl-Pmp-$Ac_6c$-Asn-NH-(3-naphthalen-1-yl-propyl) wherein "Pmp" stands for phosphonomethyl phenylalanine.

9. The method of claim 1, wherein PTI is a phenylalanyl radical having a phenyl ring, an amine end, and a carboxyl end, the phenyl ring having one or more substituents selected from the group consisting of hydroxyl, carboxyl, formyl, carboxy $C_1$–$C_6$ alkyl, carboxy $C_1$–$C_6$ alkyloxy, dicarboxy $C_1$–$C_6$ alkyl, dicarboxy $C_1$–$C_6$ alkyloxy, dicarboxyhalo $C_1$–$C_6$ alkyl, dicarboxyhalo $C_1$–$C_6$ alkyloxy, and phosphono $C_1$–$C_6$ alkyl, phosphonohalo $C_1$–$C_6$ alkyl, wherein the alkyl portion of the substituents may be unsubstituted or substituted with a substituent selected from the group consisting of halo, hydroxy, carboxyl, amino, aminoalkyl, $C_1$–$C_6$ alkyl, $C_1$–$C_6$ alkoxy, and keto;

X is a moiety attached to the nitrogen of PTI and is selected from the group consisting of $C_2$–$C_6$ alkylcarbonyl, oxalyl, $C_1$–$C_6$ alkylaminooxalyl, arylaminooxalyl, aryl $C_1$–$C_6$ alkylaminooxalyl, $C_1$–$C_6$ alkoxyoxalyl, carboxy $C_1$–$C_6$ alkyl carbonyl, heterocyclyl carbonyl, heterocyclyl $C_1$–$C_6$ alkyl carbonyl, aryl $C_1$–$C_6$ alkyl heterocyclyl $C_1$–$C_6$ alkyl carbonyl, aryloxycarbonyl, and aryl $C_1$–$C_6$ alkoxycarbonyl, wherein the aryl and alkyl portions of the substituents may be unsubstituted or substituted with a substituent selected from the group consisting of halo, hydroxy, carboxyl, amino, amino $C_1$–$C_6$ alkyl, $C_1$–$C_6$ alkyl, $C_1$–$C_6$ alkoxy, and keto; and the heterocyclyl portion of X contains at least 4 hetero atoms selected from the group consisting of O, N, and S;

AA is an amino acid, the amine end of which is attached to the carboxyl end of PTI, and Y is an aryl $C_1$–$C_6$ alkylamino or arylheterocyclyl $C_1$–$C_6$ alkylamino;

or a salt thereof.

10. The method of claim 9, wherein PTI is of the formula II:

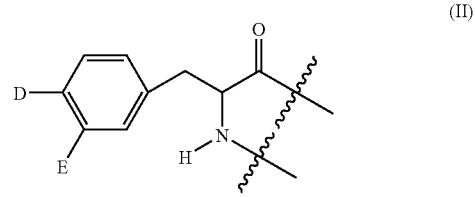

wherein D is formula (III), (IV), or (V):

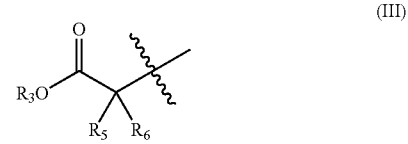

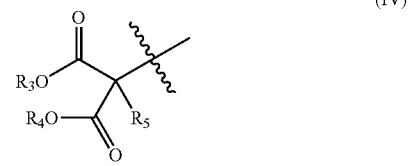

wherein $R_3$ and $R_4$ may be the same or different and are selected from the group consisting of hydrogen, $C_1$–$C_6$ alkyl, aryl, aryl $C_1$–$C_6$ alkyl, $C_1$–$C_6$ alkaryl, and heteroaryl; and $R_5$ and $R_6$ may be the same or different and are selected from the group consisting of hydrogen, halo, hydroxy, amino, and $C_1$–$C_6$ alkoxy; and E is selected from the group consisting of hydrogen, $C_1$–$C_6$ alkyl, $C_1$–$C_6$ alkylcarbonyl, carboxyl, and $C_1$–$C_6$ alkylcarbonyl $C_1$–$C_6$ alkyl.

11. The method of claim 9, wherein Y is aryl $C_1$–$C_6$ alkylamino.

12. The method of claim 11, wherein the aryl portion of Y is:

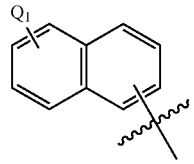

wherein $Q_1$ is hydrogen or a substituent selected from the group consisting of hydroxyl, halo, $C_1$–$C_6$ alkyl, $C_1$–$C_6$ alkoxy, amino, and $C_1$–$C_6$ acylamino.

13. The method of claim 11, wherein the heterocyclyl portion of Y is:

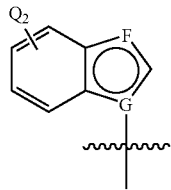

wherein $Q_2$ is hydrogen or a substituent selected from the group consisting of hydroxyl, halo, $C_1$–$C_6$ alkyl $C_1$–$C_6$ alkoxy, amino, and $C_1$–$C_6$ acylamino, and F and G are independently selected from the group consisting of C, N, O, and S.

14. The method of claim 9, wherein X is selected from the group consisting of oxalyl, $C_1$–$C_6$ alkylaminooxalyl, arylaminooxalyl, aryl $C_1$–$C_6$ alkylaminooxalyl, $C_1$–$C_6$ alkoxyoxalyl, carboxymethylcarbonyl, tetrazolylcarbonyl, tetazolylmethylcarbonyl, aminophenylmethoxycarbonyl, amino naphthyloxycarbonyl, and methoxyphenylmethyl tetrazolylmethylcarbonyl.

15. The method of claim 1, wherein said peptide is (N-oxalyl-4-malonyl)-Phe-Ac$_6$c-Asn-NH-(3-naphthalen-1-yl-propyl) or (N-acetyl-4-malonyl)-Phe-Ac$_6$c-Asn-NH-(3-naphthalen-1-yl-propyl).

16. The method of claim 1, wherein the peptide blocks HGF-stimulated cellular matrix invasion.

17. The method of claim 1, wherein the peptide blocks HGF-stimulated branching tubulogenesis.

18. The method of claim 1, wherein the peptide blocks HGF, VEGF, or bFGF-stimulated migration.

19. The method of claim 1, wherein the peptide blocks HGF, VEGF, or bFGF-stimulated cell proliferation.

20. The method of claim 1, wherein the peptide blocks HGF, VEGF, or bFGF-stimulated formation of capillary structures.

21. The method of claim 2, wherein said angiogenesis is induced by the hepatocyte growth factor (HGF).

22. A method of inhibiting angiogenesis in a mammal comprising administering to said mammal a peptide of formula (I) having cell signal inhibiting activity and cell motility inhibiting activity, wherein said peptide is substantially free of cytotoxicity:

wherein X is a group that modifies an amino group to an amide, wherein PTI is a bivalent radical of tyrosine or a bivalent radical of phosphotyrosine or of a phosphotyrosine mimetic in the form of a bivalent radical of an amino acid selected from the group consisting of phosphonomethyl-phenylalanine, phosphono-(α-fluoro)methyl-phenylalanine, phosphono-(α,α-difluoro)methylphenylalanine, phosphono-(α-hydroxy)methylphenylalanine, O-sulfotyrosine, dicarboxymethoxyphenylalanine, aspartic acid, glutamic acid, phosphoserine and phosphothreonine, each of which is present in the (D,L)-, D- or L-form;

-(AA)$_n$- is a bivalent radical of a tripeptide of the formula -(AA$^1$)-(AA$^2$)-(AA$^3$)-, wherein -(AA$^1$)- is selected from the group consisting of -Ile-, -Ac$_5$c-, -Ac$_6$c-, -Asp-, -Gly-, -Phe-, -Ac$_7$c-, -Nbo-, -Met-, -Pro-, -β-Ala-, -Gln-, -Glu-, -DHph-, -HPh- and -tLe-; -(AA$^2$)- is selected from the group consisting of -Asn-, -β-Ala-, -Gly-, -Ile-, and -Gln-; and -(AA$^3$)- is selected from the group consisting of -Val-, -β-Ala-, -Gly-, -Gln-, -Asp- and Ac$_5$c-; a bivalent radical of a dipeptide of the formula -(AA$^1$)-(AA$^2$)- wherein -(AA$^1$) and -(AA$^2$)- are as recited above;

or a bivalent radical of an amino acid selected from the amino acids mentioned above; and Y is a monosubstituted amino selected from the group consisting of lower alkylamino, octylamino, halonaphthyloxy-lower alkylamino, naphthyloxy-lower alkylamino, phenyl-lower alkylamino, di-phenyl-lower alkylamino, (mono- or di-halo-phenyl-lower alkylamino, naphthalenyl-lower alkylamino, phenanthrenyl-lower alkyl amino; cycloalkylamino; and cycloalkyl-lower alkylamino;

or a salt thereof.

23. The method of claim 22, wherein X is a moiety attached to the nitrogen of PTI and is selected from the group consisting of $C_1$–$C_6$ alkylcarbonyl, oxalyl, $C_1$–$C_6$, alkylaminooxalyl, arylaminooxalyl, aryl $C_1$–$C_6$, alkylaminooxalyl, $C_1$–$C_6$ alkoxyoxalyl, carboxy $C_1$–$C_6$ alkyl carbonyl, heterocyclyl carbonyl, heterocyclyl $C_1$–$C_6$ alkyl carbonyl, aryl $C_1$–$C_6$, alkyl heterocyclyl $C_1$–$C_6$ alkyl carbonyl, aryloxycarbonyl, and aryl $C_1$–$C_6$ alkoxycarbonyl.

24. The method of claim 22, wherein X is oxalyl.

25. The method of claim 22, wherein said peptide is selected from the group consisting of oxalyl-Pmp-Ile-Asn-NH-(3-naphthalen-1-yl-propyl), oxalyl-Pmp-Ile-Asn-NH-(3-naphthalen-2-yl-propyl), and oxalyl-Pmp-Ac$_6$c-Asn-NH-(3-naphthalen-1-yl-propyl) wherein "Pmp" stands for phosphonomethyl phenylalanine.

26. The method of claim 2, wherein

PTI is a phenylalanyl radical having a phenyl ring, an amine end, and a carboxyl end, the phenyl ring having one or more substituents selected from the group consisting of hydroxylcarboxyl, formyl, carboxy $C_1$–$C_6$ alkyl, carboxy $C_1$–$C_6$ alkyloxy, dicarboxy $C_1$–$C_6$ alkyl, dicarboxy $C_1$–$C_6$ alkyloxy, dicarboxyhalo $C_1$–$C_6$ alkyl, dicarboxyhalo $C_1$–$C_6$ alkyloxy, and phosphono $C_1$–$C_6$ alkyl, phosphonohalo $C_1$–$C_6$ alkyl, wherein the alkyl portion of the substituents may be unsubstituted or substituted with a substituent selected from the group consisting of halo, hydroxy, carboxyl, amino, aminoalkyl, $C_1$–$C_6$ alkyl, $C_1$–$C_6$ alkoxy, and keto;

X is a moiety attached to the nitrogen of PTI and is selected from the group consisting of $C_1$–$C_6$ alkylcarbonyl, oxalyl, $C_1$–$C_6$ alkylaminooxalyl, arylaminooxalyl, aryl $C_1$–$C_6$ alkylaminooxalyl, $C_1$–$C_6$ alkoxyoxalyl, carboxy $C_1$–$C_6$ alkyl carbonyl, heterocyclyl carbonyl, heterocyclyl $C_1$–$C_6$ alkyl carbonyl aryl $C_1$–$C_6$ alkyl heterocyclyl $C_1$–$C_6$ alkyl carbonyl, aryloxycarbonyl, and aryl $C_1$–$C_6$ alkoxycarbonyl, wherein the aryl and alkyl portions of the substituents may be unsubstituted or substituted with a substituent selected from the group consisting of halo, hydroxy, carboxyl, amino, amino $C_1$–$C_6$ alkyl, $C_1$–$C_6$ alkyl, $C_1$–$C_6$ alkoxy, and keto; and the heterocyclyl portion of X contains at least 4 hetero atoms selected from the group consisting of O, N, and S;

AA is an amino acid, the amine end of which is attached to the carboxyl end of PTI; and Y is an aryl $C_1$–$C_6$ alkylamino or arylheterocyclyl $C_1$–$C_6$ alkylamino;

or a salt thereof.

27. The method of claim 26, wherein PTI is of the formula II:

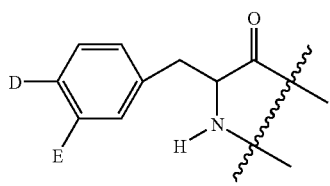

(II)

wherein D is formula (III), (IV), or (V):

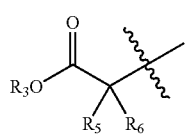

(III)

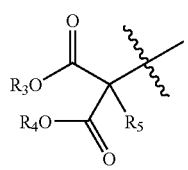

(IV)

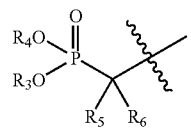

(V)

wherein $R_3$ and $R_4$ may be the same or different and are selected from the group consisting of hydrogen $C_1$–$C_6$ alkyl, aryl, aryl $C_1$–$C_6$ alkyl, $C_1$–$C_6$ alkaryl, and heteroaryl; and $R_5$ and $R_6$ may be the same or different and are selected from the group consisting of hydrogen, halo, hydroxy, amino, and $C_1$–$C_6$ alkoxy; and E is selected from the group consisting of hydrogen, $C_1$–$C_6$ alkyl, $C_1$–$C_6$ alkylcarbonyl, carboxyl, and $C_1$–$C_6$ alkylcarbonyl $C_1$–$C_6$ alkyl.

28. The method of claim 26, wherein Y is aryl $C_1$–$C_6$ alkylamino.

29. The method of claim 2, wherein said peptide is (N-oxalyl-4-malonyl)-Phe-Ac$_6$c-Asn-NH-(3-naphthalen-1-yl-propyl) or (N-acetyl-4-malonyl)-Phe-Ac$_6$c-Asn-NH-(3-naphthalen-1-yl-propyl).

30. The method of claim 15, wherein said peptide is (N-oxalyl-4-malonyl)-Phe-Ac$_6$c-Asn-NH-(3-naphthalen-1-yl-propyl).

31. The method of claim 29, wherein said peptide is (N-oxalyl-4-malonyl)-Phe-Ac$_6$c-Asn-NH-(3-naphthalen-1-yl-propyl).

32. The method of claim 26, wherein the aryl portion of Y is:

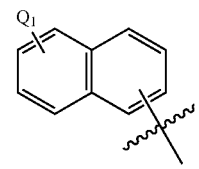

wherein $Q_1$ is hydrogen or a substituent selected from the group consisting of hydroxyl, halo, $C_1$–$C_6$ alkyl, $C_1$–$C_6$ alkoxy, amino, and $C_1$–$C_6$ acylamino.

33. The method of claim 26, wherein the heterocyclyl portion of Y is:

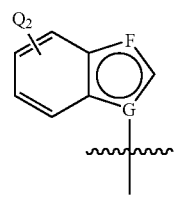

wherein $Q_2$ is hydrogen or a substituent selected from the group consisting of hydroxyl halo, $C_1$–$C_6$ alkyl, $C_1$–$C_6$ alkoxy, amino, and $C_1$–$C_6$ acylamino, and F and G are independently selected from the group consisting of C, N, O, and S.

34. The method of claim 26, wherein X is selected from the group consisting of acetyl, oxalyl, $C_1$–$C_6$ alkylaminooxalyl, arylaminooxalyl, aryl $C_1$–$C_6$ alkylaminooxalyl, $C_1$–$C_6$ alkoxyoxalyl, carboxymethylcarbonyl, tetrazolylcarbonyl, tetrazolylmethylcarbonyl, aminophenylmethoxycarbonyl, amino naphthyloxycarbonyl, and methoxyphenylmethyl tetrazolylmethylcarbonyl.

35. The method of claim 2, wherein said angiogenesis is one that is induced by the hepatocyte growth factor (HGF).

36. The method of claim 2, wherein n is 1–3.

* * * * *